US008263651B2

(12) United States Patent
Hammock et al.

(10) Patent No.: US 8,263,651 B2
(45) Date of Patent: Sep. 11, 2012

(54) USE OF CIS-EPOXYEICOSATRIENOIC ACIDS AND INHIBITORS OF SOLUBLE EPOXIDE HYDROLASE TO TREAT CONDITIONS MEDIATED BY PBR, CB2, AND NK2 RECEPTORS

(75) Inventors: Bruce D. Hammock, Davis, CA (US); Ahmet Bora Inceoglu, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 273 days.

(21) Appl. No.: 12/518,549

(22) PCT Filed: Jan. 4, 2007

(86) PCT No.: PCT/US2007/000373

§ 371 (c)(1), (2), (4) Date: Oct. 27, 2009

(87) PCT Pub. No.: WO2008/073130

PCT Pub. Date: Jun. 19, 2008

(65) Prior Publication Data

US 2010/0074852 A1 Mar. 25, 2010

Related U.S. Application Data

(60) Provisional application No. 60/875,039, filed on Dec. 15, 2006.

(51) Int. Cl.
*A61K 31/34* (2006.01)

(52) U.S. Cl. ....................................................... 514/475

(58) Field of Classification Search .................... 514/44, 514/475

See application file for complete search history.

(56) References Cited

U.S. PATENT DOCUMENTS

| | | | |
|---|---|---|---|
| 5,955,496 | A | 9/1999 | Hammock et al. |
| 6,150,415 | A | 11/2000 | Hammock et al. |
| 6,174,695 | B1 | 1/2001 | Hammock et al. |
| 6,531,506 | B1 | 3/2003 | Kroetz et al. |
| 6,630,602 | B1 | 10/2003 | Bialer et al. |
| 2004/0092567 | A1 | 5/2004 | Ingraham et al. |
| 2005/0026844 | A1 | 2/2005 | Hammock et al. |
| 2005/0261255 | A1 | 11/2005 | Serhan et al. |
| 2006/0148744 | A1 | 7/2006 | Hammock et al. |
| 2006/0178347 | A1 | 8/2006 | Hammock et al. |

FOREIGN PATENT DOCUMENTS

WO WO 2006/133257 A2 12/2006

OTHER PUBLICATIONS

Enouch et al. Am Fam Physician 2002;65:441-8,449-50. Copyright© 2002 American Academy of Family Physicians.).*

Fisher et al. Psychiatric Bulletin (2003); 27:446-448.*

Pacifici et al; Arch Toxicol (1989):157-159.*

Robbins et al. Br. J. Clin. Pharmac (1990); 29, 759-762.* www.arabidopsis.org/servlets/TairObject.*

Kim et al. J. Med. Chem. 2005, 48, 3621-3629.*

Inceoglu et al.; "Soluble epoxide hydrolase inhibition reveals novel biological functions of epoxyeicosatrienoic acids (EETs)"; 2007; *Prostaglandins & other Lipid Mediators*; 82:42-49.

Zavala, Flora; "Benzodiazepines, Anxiety and Immunity"; 1997; *Pharmacological Therapy*; 75(3):199-216.

Kathurita Satish et al, "Modulation of anxiety through blockade of anandamide hydrolysis", Nature Medicine, Jan. 2003, vol. 9, No. 1, pp. 76-81.

Shen Min et al., "Application of predictive QSAR models to database mining: identification and experimental validation of novel anticonvulsant compounds", Journal of Medicinal Chemistry Apr. 22, 2004, vol. 47, No. 9, pp. 2356-2364.

Imig John D, "Cardiovascular therapeutic aspects of soluble epoxide hydrolase inhibitors", Cardiovascular Drug Reviews Summer 2006, vol. 24, No. 2, Jul. 2006, pp. 169-188.

Fang Xiang, "Soluble epoxide hydrolase: A Novel Target for the Treatment of Hypertension", Recent patents on cardiovascular drug discovery, Jan. 2006, vol. 1, pp. 67-72.

Morisseau C. et al., "Potent urea and carbamate inhibitors of soluble epoxide hydrolases", Proceedings of the National Academy of Sciences of the United States of America, Aug. 3, 1999, vol. 96, No. 16, pp. 8849-8854.

Europen Search Report for PCT/US2007/000373 mailed Dec. 2, 2010.

Cunningham, et al., Neuropharmacology. (2003) 45(7):907-17, abstract only.

Johannessen, Neurochem Int. (2000) 37(2-3):103-10, abstract only.

Löscher, CNS Drugs. (2002) 16(10):669-94, abstract only.

Perucca, CNS Drugs. (2002) 16(10):695-714, abstract only.

Owens and Nemeroff, Psychopharmacol Bull. (2003) 37 Suppl 2:17-24, abstract only.

Eickholt, et al., Mol Pharmacol. (2005) 67(5): 1426-1433.

* cited by examiner

*Primary Examiner* — Brandon Fetterolf
*Assistant Examiner* — Shirley V Gembeh
(74) *Attorney, Agent, or Firm* — Weaver Austin Villeneuve and Sampson LLP

(57) ABSTRACT

The invention relates to the discovery that cis-epoxyeicosatraenoic acids (EETs) bind to and act as agonists of peripheral benzodiazepine receptor and the cannabinoid $CB_2$ receptor. The invention provides methods of reducing symptoms of conditions whose activity is mediated by these receptors, including inhibiting anxiety, inhibiting the growth of cancer cells expressing peripheral benzodiazepine receptors, and reducing oxygen radical damage to cells, by contacting the cells with a cis-epoxyeicosantrienoic acid, an inhibitor of soluble epoxide hydrolase (sEH), or both. The invention further provides methods of inhibiting irritable bowel syndrome by administering to individuals with inhibiting irritable bowel syndrome a cis-epoxyeicosantrienoic acid, an inhibitor of soluble epoxide hydrolase (sEH), or both. In some embodiments, the method comprises administering to the individual a nucleic acid which inhibits expression of sEH.

19 Claims, 5 Drawing Sheets

```
                     SEQUENCE LISTING


<160> NUMBER OF SEQ ID NOS: 38

<210> SEQ ID NO 1
<211> LENGTH: 554
<212> TYPE: PRT
<213> ORGANISM: Homo sapiens
<220> FEATURE:
<223> OTHER INFORMATION: human soluble epoxide hydrolase (sEH)

<400> SEQUENCE: 1

Met Thr Leu Arg Gly Ala Val Phe Asp Leu Asp Gly Val Leu Ala Leu
 1               5                  10                  15

Pro Ala Val Phe Gly Val Leu Gly Arg Thr Glu Glu Ala Leu Ala Leu
            20                  25                  30

Pro Arg Gly Leu Leu Asn Asp Ala Phe Gln Lys Gly Gly Pro Glu Gly
        35                  40                  45

Ala Thr Thr Arg Leu Met Lys Gly Glu Ile Thr Leu Ser Gln Trp Ile
    50                  55                  60

Pro Leu Met Glu Glu Asn Cys Arg Lys Cys Ser Glu Thr Ala Lys Val
65                  70                  75                  80

Cys Leu Pro Lys Asn Phe Ser Ile Lys Glu Ile Phe Asp Lys Ala Ile
```

-continued

```
                85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
    210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Trp Pro Ala Val Cys Leu Cys His Gly Phe Pro Glu Ser Trp Tyr Ser
            260                 265                 270

Trp Arg Tyr Gln Ile Pro Ala Leu Ala Gln Ala Gly Tyr Arg Val Leu
        275                 280                 285

Ala Met Asp Met Lys Gly Tyr Gly Glu Ser Ser Ala Pro Pro Glu Ile
    290                 295                 300

Glu Glu Tyr Cys Met Glu Val Leu Cys Lys Glu Met Val Thr Phe Leu
305                 310                 315                 320

Asp Lys Leu Gly Leu Ser Gln Ala Val Phe Ile Gly His Asp Trp Gly
                325                 330                 335

Gly Met Leu Val Trp Tyr Met Ala Leu Phe Tyr Pro Glu Arg Val Arg
            340                 345                 350

Ala Val Ala Ser Leu Asn Thr Pro Phe Ile Pro Ala Asn Pro Asn Met
        355                 360                 365

Ser Pro Leu Glu Ser Ile Lys Ala Asn Pro Val Phe Asp Tyr Gln Leu
    370                 375                 380

Tyr Phe Gln Glu Pro Gly Val Ala Glu Ala Glu Leu Glu Gln Asn Leu
385                 390                 395                 400

Ser Arg Thr Phe Lys Ser Leu Phe Arg Ala Ser Asp Glu Ser Val Leu
                405                 410                 415

Ser Met His Lys Val Cys Glu Ala Gly Gly Leu Phe Val Asn Ser Pro
            420                 425                 430

Glu Glu Pro Ser Leu Ser Arg Met Val Thr Glu Glu Glu Ile Gln Phe
        435                 440                 445

Tyr Val Gln Gln Phe Lys Lys Ser Gly Phe Arg Gly Pro Leu Asn Trp
    450                 455                 460

Tyr Arg Asn Met Glu Arg Asn Trp Lys Trp Ala Cys Lys Ser Leu Gly
465                 470                 475                 480

Arg Lys Ile Leu Ile Pro Ala Leu Met Val Thr Ala Glu Lys Asp Phe
                485                 490                 495

Val Leu Val Pro Gln Met Ser Gln His Met Glu Asp Trp Ile Pro His
            500                 505                 510
```

```
Leu Lys Arg Gly His Ile Glu Asp Cys Gly His Trp Thr Gln Met Asp
        515                 520                 525

Lys Pro Thr Glu Val Asn Gln Ile Leu Ile Lys Trp Leu Asp Ser Asp
    530                 535                 540

Ala Arg Asn Pro Pro Val Val Ser Lys Met
545                 550


<210> SEQ ID NO 2
<211> LENGTH: 2101
<212> TYPE: DNA
<213> ORGANISM: Homo sapiens
<220> FEATURE:
<223> OTHER INFORMATION: polynucleotide encoding human soluble epoxide
      hydrolase (sEH)

<400> SEQUENCE: 2

ggcacgagct ctctctctct ctctctctct ctctcgccgc catgacgctg cgcggcgccg     60

tcttcgacct tgacggggtg ctggcgctgc cagcggtgtt cggcgtcctc ggccgcacgg    120

aggaggccct ggcgctgccc agaggacttc tgaatgatgc tttccagaaa gggggaccag    180

agggtgccac tacccggctt atgaaaggag agatcacact ttcccagtgg ataccactca    240

tggaagaaaa ctgcaggaag tgctccgaga ccgctaaagt ctgcctcccc aagaatttct    300

ccataaaaga aatctttgac aaggcgattt cagccagaaa gatcaaccgc cccatgctcc    360

aggcagctct catgctcagg aagaaaggat tcactactgc catcctcacc aacacctggc    420

tggacgaccg tgctgagaga gatggcctgg cccagctgat gtgtgagctg aagatgcact    480

ttgacttcct gatagagtcg tgtcaggtgg gaatggtcaa acctgaacct cagatctaca    540

agtttctgct ggacaccctg aaggccagcc ccagtgaggt cgttttttttg gatgacatcg    600

gggctaatct gaagccagcc cgtgacttgg gaatggtcac catcctggtc caggacactg    660

acacggccct gaaagaactg gagaaagtga ccggaatcca gcttctcaat accccggccc    720

ctctgccgac ctcttgcaat ccaagtgaca tgagccatgg gtacgtgaca gtaaagccca    780

gggtccgtct gcattttgtg gagctgggct ggcctgctgt gtgcctctgc catggatttc    840

ccgagagttg gtattcttgg aggtaccaga tccctgctct ggcccaggca ggttaccggg    900

tcctagctat ggacatgaaa ggctatggag agtcatctgc tcctcccgaa atagaagaat    960

attgcatgga agtgttatgt aaggagatgg taaccttcct ggataaactg ggcctctctc   1020

aagcagtgtt cattggccat gactggggtg gcatgctggt gtggtacatg gctctcttct   1080

accccgagag agtgagggcg gtggccagtt tgaatactcc cttcatacca gcaaatccca   1140

acatgtcccc tttggagagt atcaaagcca acccagtatt tgattaccag ctctacttcc   1200

aagaaccagg agtggctgag gctgaactgg aacagaacct gagtcggact ttcaaaagcc   1260

tcttcagagc aagcgatgag agtgttttat ccatgcataa agtctgtgaa gcgggaggac   1320

tttttgtaaa tagcccagaa gagcccagcc tcagcaggat ggtcactgag gaggaaatcc   1380

agttctatgt gcagcagttc aagaagtctg gtttcagagg tcctctaaac tggtaccgaa   1440

acatggaaag gaactggaag tgggcttgca aaagcttggg acggaagatc ctgattccgg   1500

ccctgatggt cacggcggag aaggacttcg tgctcgttcc tcagatgtcc cagcacatgg   1560

aggactggat tccccacctg aaaaggggac acattgagga ctgtgggcac tggacacaga   1620

tggacaagcc aaccgaggtg aatcagatcc tcattaagtg gctggattct gatgcccgga   1680

acccaccggt ggtctcaaag atgtagaacg cagcgtagtg cccacgctca gcaggtgtgc   1740

catccttcca cctgctgggg caccattctt agtatacaga ggtggcctta cacacatctt   1800
```

-continued

```
gcatggatgg cagcattgtt ctgaaggggt ttgcagaaaa aaaagatttt ctttacataa   1860

agtgaatcaa atttgacatt attttagatc ccagagaaat caggtgtgat tagttctcca   1920

ggcatgaatg catcgtccct ttatctgtaa gaacccttag tgtcctgtag gggacagaa    1980

tggggtggcc aggtggtgat ttctctttga ccaatgcata gtttggcaga aaaatcagcc   2040

gttcatttag aagaatctta gcagagattg ggatgcctta ctcaataaag ctaagatgac   2100

t                                                                   2101


<210> SEQ ID NO 3
<211> LENGTH: 23
<212> TYPE: DNA
<213> ORGANISM: Artificial Sequence
<220> FEATURE:
<223> OTHER INFORMATION: synthetic sEH target sequence

<400> SEQUENCE: 3

cagtgttcat tggccatgac tgg                                             23


<210> SEQ ID NO 4
<211> LENGTH: 21
<212> TYPE: DNA
<213> ORGANISM: Artificial Sequence
<220> FEATURE:
<223> OTHER INFORMATION: synthetic sEH sense siRNA

<400> SEQUENCE: 4

guguucauug gccaugacut t                                               21


<210> SEQ ID NO 5
<211> LENGTH: 21
<212> TYPE: DNA
<213> ORGANISM: Artificial Sequence
<220> FEATURE:
<223> OTHER INFORMATION: synthetic sEH antisense siRNA

<400> SEQUENCE: 5

agucauggcc aaugaacact t                                               21


<210> SEQ ID NO 6
<211> LENGTH: 23
<212> TYPE: DNA
<213> ORGANISM: Artificial Sequence
<220> FEATURE:
<223> OTHER INFORMATION: synthetic sEH target sequence

<400> SEQUENCE: 6

gaaaggctat ggagagtcat ctg                                             23


<210> SEQ ID NO 7
<211> LENGTH: 21
<212> TYPE: DNA
<213> ORGANISM: Artificial Sequence
<220> FEATURE:
<223> OTHER INFORMATION: synthetic sEH sense siRNA

<400> SEQUENCE: 7

aaggcuaugg agagucauct t                                               21


<210> SEQ ID NO 8
<211> LENGTH: 21
<212> TYPE: DNA
<213> ORGANISM: Artificial Sequence
<220> FEATURE:
<223> OTHER INFORMATION: synthetic sEH antisense siRNA
```

<400> SEQUENCE: 8
gaugacucuc cauagccuut t 21

<210> SEQ ID NO 9
<211> LENGTH: 23
<212> TYPE: DNA
<213> ORGANISM: Artificial Sequence
<220> FEATURE:
<223> OTHER INFORMATION: synthetic sEH target sequence

<400> SEQUENCE: 9
aaaggctatg gagagtcatc tgc 23

<210> SEQ ID NO 10
<211> LENGTH: 21
<212> TYPE: DNA
<213> ORGANISM: Artificial Sequence
<220> FEATURE:
<223> OTHER INFORMATION: synthetic sEH sense siRNA

<400> SEQUENCE: 10
aggcuaugga gagucaucut t 21

<210> SEQ ID NO 11
<211> LENGTH: 21
<212> TYPE: DNA
<213> ORGANISM: Artificial Sequence
<220> FEATURE:
<223> OTHER INFORMATION: synthetic sEH antisense siRNA

<400> SEQUENCE: 11
agaugacucu ccauagccut t 21

<210> SEQ ID NO 12
<211> LENGTH: 23
<212> TYPE: DNA
<213> ORGANISM: Artificial Sequence
<220> FEATURE:
<223> OTHER INFORMATION: synthetic sEH target sequence

<400> SEQUENCE: 12
caagcagtgt tcattggcca tga 23

<210> SEQ ID NO 13
<211> LENGTH: 21
<212> TYPE: DNA
<213> ORGANISM: Artificial Sequence
<220> FEATURE:
<223> OTHER INFORMATION: synthetic sEH sense siRNA

<400> SEQUENCE: 13
agcaguguuc auuggccaut t 21

<210> SEQ ID NO 14
<211> LENGTH: 21
<212> TYPE: DNA
<213> ORGANISM: Artificial Sequence
<220> FEATURE:
<223> OTHER INFORMATION: synthetic sEH antisense siRNA

<400> SEQUENCE: 14
auggccaaug aacacugcut t 21

<210> SEQ ID NO 15
<211> LENGTH: 23
<212> TYPE: DNA

<213> ORGANISM: Artificial Sequence
<220> FEATURE:
<223> OTHER INFORMATION: synthetic sEH target sequence

<400> SEQUENCE: 15
cagcacatgg aggactggat tcc 23

<210> SEQ ID NO 16
<211> LENGTH: 21
<212> TYPE: DNA
<213> ORGANISM: Artificial Sequence
<220> FEATURE:
<223> OTHER INFORMATION: synthetic sEH sense siRNA

<400> SEQUENCE: 16
gcacauggag gacuggauut t 21

<210> SEQ ID NO 17
<211> LENGTH: 21
<212> TYPE: DNA
<213> ORGANISM: Artificial Sequence
<220> FEATURE:
<223> OTHER INFORMATION: synthetic sEH antisense siRNA

<400> SEQUENCE: 17
aauccagucc uccaugugct t 21

<210> SEQ ID NO 18
<211> LENGTH: 9
<212> TYPE: DNA
<213> ORGANISM: Artificial Sequence
<220> FEATURE:
<223> OTHER INFORMATION: synthetic spacer sequence

<400> SEQUENCE: 18 ttcaagaga 9

<210> SEQ ID NO 19
<211> LENGTH: 23
<212> TYPE: DNA
<213> ORGANISM: Artificial Sequence
<220> FEATURE:
<223> OTHER INFORMATION: synthetic siRNA target sequence

<400> SEQUENCE: 19
cagtgttcat tggccatgac tgg 23

<210> SEQ ID NO 20
<211> LENGTH: 59
<212> TYPE: DNA
<213> ORGANISM: Artificial Sequence
<220> FEATURE:
<223> OTHER INFORMATION: synthetic sense siRNA hairpin sequence

<400> SEQUENCE: 20
gatccccgtg ttcattggcc atgactttca agagaagtca tggccaatga acactttttt 59

<210> SEQ ID NO 21
<211> LENGTH: 59
<212> TYPE: DNA
<213> ORGANISM: Artificial Sequence
<220> FEATURE:
<223> OTHER INFORMATION: synthetic antisense siRNA hairpin sequence

<400> SEQUENCE: 21
agctaaaaag tgttcattgg ccatgacttc tcttgaaagt catggccaat gaacacggg 59

-continued

<210> SEQ ID NO 22
<211> LENGTH: 23
<212> TYPE: DNA
<213> ORGANISM: Artificial Sequence
<220> FEATURE:
<223> OTHER INFORMATION: synthetic siRNA target sequence

<400> SEQUENCE: 22
gaaaggctat ggagagtcat ctg 23

<210> SEQ ID NO 23
<211> LENGTH: 59
<212> TYPE: DNA
<213> ORGANISM: Artificial Sequence
<220> FEATURE:
<223> OTHER INFORMATION: synthetic sense siRNA hairpin sequence

<400> SEQUENCE: 23
gatccccaag gctatggaga gtcatcttca agagagatga ctctccatag ccttttttt 59

<210> SEQ ID NO 24
<211> LENGTH: 59
<212> TYPE: DNA
<213> ORGANISM: Artificial Sequence
<220> FEATURE:
<223> OTHER INFORMATION: synthetic antisense siRNA hairpin sequence

<400> SEQUENCE: 24
agctaaaaaa aggctatgga gagtcatctc tcttgaagat gactctccat agccttggg 59

<210> SEQ ID NO 25
<211> LENGTH: 23
<212> TYPE: DNA
<213> ORGANISM: Artificial Sequence
<220> FEATURE:
<223> OTHER INFORMATION: synthetic siRNA target sequence

<400> SEQUENCE: 25
aaaggctatg gagagtcatc tgc 23

<210> SEQ ID NO 26
<211> LENGTH: 59
<212> TYPE: DNA
<213> ORGANISM: Artificial Sequence
<220> FEATURE:
<223> OTHER INFORMATION: synthetic sense siRNA hairpin sequence

<400> SEQUENCE: 26
gatccccagg ctatggagag tcatctttca agagaagatg actctccata gccttttt 59

<210> SEQ ID NO 27
<211> LENGTH: 59
<212> TYPE: DNA
<213> ORGANISM: Artificial Sequence
<220> FEATURE:
<223> OTHER INFORMATION: synthetic antisense siRNA hairpin sequence

<400> SEQUENCE: 27
agctaaaaaa ggctatggag agtcatcatc tcttgaaaga tgactctcca tagcctggg 59

<210> SEQ ID NO 28
<211> LENGTH: 23
<212> TYPE: DNA
<213> ORGANISM: Artificial Sequence
<220> FEATURE:
<223> OTHER INFORMATION: synthetic siRNA target sequence

<400> SEQUENCE: 28
caagcagtgt tcattggcca tga                                      23

<210> SEQ ID NO 29
<211> LENGTH: 59
<212> TYPE: DNA
<213> ORGANISM: Artificial Sequence
<220> FEATURE:
<223> OTHER INFORMATION: synthetic sense siRNA hairpin sequence

<400> SEQUENCE: 29
gatccccagc agtgttcatt ggccatttca agagaatggc caatgaacac tgctttttt      59

<210> SEQ ID NO 30
<211> LENGTH: 59
<212> TYPE: DNA
<213> ORGANISM: Artificial Sequence
<220> FEATURE:
<223> OTHER INFORMATION: synthetic antisense siRNA hairpin sequence

<400> SEQUENCE: 30
agctaaaaaa gcagtgttca ttggccattc tcttgaaatg gccaatgaac actgctggg      59

<210> SEQ ID NO 31
<211> LENGTH: 23
<212> TYPE: DNA
<213> ORGANISM: Artificial Sequence
<220> FEATURE:
<223> OTHER INFORMATION: synthetic siRNA target sequence

<400> SEQUENCE: 31
cagcacatgg aggactggat tcc                                      23

<210> SEQ ID NO 32
<211> LENGTH: 59
<212> TYPE: DNA
<213> ORGANISM: Artificial Sequence
<220> FEATURE:
<223> OTHER INFORMATION: synthetic sense siRNA hairpin sequence

<400> SEQUENCE: 32
gatccccgca catggaggac tggattttca agagaaatcc agtcctccat gtgctttt       59

<210> SEQ ID NO 33
<211> LENGTH: 59
<212> TYPE: DNA
<213> ORGANISM: Artificial Sequence
<220> FEATURE:
<223> OTHER INFORMATION: synthetic antisense siRNA hairpin sequence

<400> SEQUENCE: 33
agctaaaaag cacatggagg actggatttc tcttgaaaat ccagtcctcc atgtgcggg      59

<210> SEQ ID NO 34
<211> LENGTH: 20
<212> TYPE: RNA
<213> ORGANISM: Artificial Sequence
<220> FEATURE:
<223> OTHER INFORMATION: synthetic antisense sEH sequence

<400> SEQUENCE: 34
uguccagugc ccacaguccu                                         20

<210> SEQ ID NO 35
<211> LENGTH: 20
<212> TYPE: RNA

-continued

```
<213> ORGANISM: Artificial Sequence
<220> FEATURE:
<223> OTHER INFORMATION: synthetic antisense sEH sequence

<400> SEQUENCE: 35

uucccaccug acacgacucu                                              20


<210> SEQ ID NO 36
<211> LENGTH: 20
<212> TYPE: RNA
<213> ORGANISM: Artificial Sequence
<220> FEATURE:
<223> OTHER INFORMATION: synthetic antisense sEH sequence

<400> SEQUENCE: 36

guucagccuc agccacuccu                                              20


<210> SEQ ID NO 37
<211> LENGTH: 19
<212> TYPE: RNA
<213> ORGANISM: Artificial Sequence
<220> FEATURE:
<223> OTHER INFORMATION: synthetic antisense sEH sequence

<400> SEQUENCE: 37

aguccucccg cuucacaga                                               19


<210> SEQ ID NO 38
<211> LENGTH: 21
<212> TYPE: RNA
<213> ORGANISM: Artificial Sequence
<220> FEATURE:
<223> OTHER INFORMATION: synthetic antisense sEH sequence

<400> SEQUENCE: 38

gcccacuucc aguuccuuuc c                                            21
```

USE OF CIS-EPOXYEICOSATRIENOIC ACIDS AND INHIBITORS OF SOLUBLE EPOXIDE HYDROLASE TO TREAT CONDITIONS MEDIATED BY PBR, CB2, AND NK2 RECEPTORS

CROSS-REFERENCES TO RELATED APPLICATIONS

This application is the U.S. National Stage entry of International Application No. PCT/US2007/000373, filed Jan. 4, 2007, which claims priority from and benefit of U.S. Provisional Application No. 60/875,039, filed Dec. 15, 2006; the contents of each are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. ES02710, awarded by the NIH. The Government has certain rights in this invention.

REFERENCE TO A “SEQUENCE LISTING,” A TABLE, OR A COMPUTER PROGRAM LISTING APPENDIX SUBMITTED ON A COMPACT DISK

Not applicable

BACKGROUND OF THE INVENTION

It would be useful to have additional methods of decreasing anxiety, inhibiting the proliferation of cancer cells, of reducing irritable bowel syndrome, and of increasing endogenous neurosteroid production.

The present invention fills these and other needs.

BRIEF SUMMARY OF THE INVENTION

In a first group of embodiments, the invention provide methods of relieving symptoms of a condition selected from the group consisting of anxiety, panic attack, agitation, status epilepticus, other forms of epilepsy, alcohol or opiate withdrawal, insomnia, or mania in a subject in need thereof, by administering to the subject an effective amount of an agent or agents selected from the group consisting of a cis-epoxyeicosantrienoic acid (“EET”), an inhibitor of soluble epoxide hydrolase (“sEH”), and a combination of an EET and an inhibitor of sEH, thereby relieving the symptoms of the condition in the subject. In some embodiments, the agent is an EET. In some embodiments, the EET is selected from the group consisting of 14,15-BET, 8,9-EET, 11,12-EET or 5,6-EET. In some embodiments, the agent is an inhibitor of sEH. In some embodiments, the condition is anxiety.

In a further group of embodiments, the invention provides methods of inhibiting growth of cancer cells expressing peripheral benzodiazepine receptors (PBR) or $CB_2$ receptors. The methods comprise contacting said cells with an effective amount of an agent or agents selected from the group consisting of a cis-epoxyeicosantrienoic acid (“EET”), an inhibitor of soluble epoxide hydrolase (“sEH”), and a combination of an EET and an inhibitor of sEH, thereby inhibiting the growth of the cancer cells. In some embodiments, the cancer cells are glioma cells. In some embodiments, the cells are astrocytoma cells. In some embodiments, the cells are breast cancer cells. In some embodiments, the agent is an EET. In some embodiments, the EET is selected from the group consisting of 14,15-EET, and 11,12-BET. In some embodiments, the agent is an inhibitor of sEH. In some embodiments, the EET or the inhibitor of sEH, or both, are contained in a material which releases the EET or the inhibitor, or both, over time.

In yet a further group of embodiments, the invention provides methods of reducing oxygen radical damage to cells. The methods comprise contacting said cells with an effective amount of an agent or agents selected from the group consisting of a cis-epoxyeicosantrienoic acid (“EET”), an inhibitor of soluble epoxide hydrolase (“sEH”), and a combination of an EET and an inhibitor of sEH, thereby reducing oxygen radical damage to the cells. In some embodiments, the agent is an EET. In some embodiments, the EET is selected from the group consisting of 14,15-BET, 8,9-EET and 11,12-EET. In some embodiments, the agent is an inhibitor of sEH. In some embodiments, the EET, or said inhibitor of sEH, or both, are administered by applying to the skin a topical formulation comprising the EET or the inhibitor of sEH, or both. In some embodiments, the topical formulation further comprises a sunscreen or sunblock.

In still a further group of embodiments, the invention provides methods of relieving symptoms of irritable bowel syndrome (IBS) in a subject in need thereof. The method comprises administering to the subject an effective amount of an agent or agents selected from the group consisting of a cis-epoxyeicosantrienoic acid (“EET”), an inhibitor of soluble epoxide hydrolase (“sEH”), and a combination of an EET and an inhibitor of sEH, thereby relieving symptoms of IBS in the subject. In some embodiments, the agent is an EET. In some embodiments, the EET is selected from the group consisting of 14,15-EET, 8,9-EET, and 11,12-EET. In some embodiments, the agent is an inhibitor of sEH.

BRIEF DESCRIPTION OF THE DRAWINGS

FIG. 2A shows the effect on animals administered the steroid synthesis inhibitor aminogluthetimide (“AGL”), while FIG. 2B shows the effect of animals administered the steroid synthesis inhibitor finasteride (“FIN”). FIG. 2C shows that show that AGL and FIN by themselves have no impact on the baseline response shown by control animals, which FIG. 2D shows that they do not they modify the response of animals to LPS administration. For each of FIGS. 2A-D, the Y axis shows hindpaw thermal withdrawal latencies (“TWL”) of the animals in the study reported in the Figure as a percentage of TWL prior to any treatment (“Baseline”). The X axis shows the various points in time at which measurements of TWL were taken. “BL” means starting (“base line”) measurement taken before administration of agents to the animals. FIG. 2A: Hollow diamonds: animals treated only with lipopolysaccharide (“LPS”) (n=16). “X” with vertical line: animals treated with LPS+an inhibitor of sEH called “AEPU” (n=6). “X”: animals treated with LPS and AGL (n=6). “+” sign: animals treated with AGL, LPS, and AEPU (n=7). FIG. 2B: Hollow diamonds: animals treated only with LPS (n=16) (same data as in FIG. 2A). "X" with vertical line: animals treated with LPS+an inhibitor of sEH called "AEPU" (n=6) (same data as in FIG. 2A). "X": animals treated with LPS and FIN (n=6). "+" sign: animals treated with FIN, LPS, and AEPU (n=8). FIG. 2C: Filled diamonds: control (untreated) animals (n=6). Filled squares: animals treated with AEPU, but not LPS (n=6). Filled triangles: animals treated with AGL, but not LPS (n=4). "X": animals treated with FIN, but not LPS (n=4). FIG. 2D: Filled diamonds: animals treated only with LPS (n=16) (data as in FIGS. 2A and B). Filled squares: animals treated with LPS and AGL (n=6). Hollow triangles: animals treated with LPS and FIN (n=6).

(In FIG. 3A, the bar presenting the results for the metabolite 6-keto-PGF1a for one group of animals exceeded the scale, as shown by a break in the bar and the statement of the result in ng/mL about the bar). FIG. 3A. This graph shows the amounts of the sum of the vic-dihydroxyeicosatrienoic acids ("DHETs"), the sum of the EETs, 6-keto-PGF1a, PGF2a, and PGE2 in untreated ("naive") animals, in animals treated with lipopolysaccharide ("LPS"), in animals treated with LPS and an inhibitor of sEH referred to as AEPU, and in animals treated with LPS, AEPU, and aminogluthetimide ("AGL") FIG. 3B. This graph shows the relative amounts of the sum of the metabolite DiHOMEs (diols of linoleate epoxide), the sum of the metabolites EpOMEs (linoleic acid mono-epoxides) and of the metabolite thromboxane $B_2$ ("TxB2") in the four groups of animals described with regard to FIG. 3A. FIG. 3C. This graph shows the amounts of the sum of the hydroxyoctadecadienoic acids ("HODEs") and the sum of the hydroxyeicosatetraenoic acids ("HETEs") in the four groups of animals described with regard to FIG. 3A. All three graphs: bars with lines rising from left to right (e.g., in FIG. 3A, the "sum of DHETs") present results for untreated (naïve) animals, bars with lines falling from left to right present results for animals treated with LPS, bars with cross-hatching present results for the animals treated with LPS and the sEH inhibitor AEPU, and bars with horizontal lines present the results for animals treated with LPS, AEPU, and the steroid synthesis inhibitor aminogluthetimide ("AGL"). The metabolites chosen for study show the effect on different pathways by which arachidonic acid is metabolized. ΣEpOMEs and ΣDiHOMEs are indicators of the P450 pathway, HETEs are an indicator of how much arachidonic acid is going through the 5-lipoxygenase pathway and 6-keto-$PGF_{1a}$, and $PGE_2$ are indicators of the arachidonic acid metabolized by the cyclooxygenase pathway. 6-keto-$PGF_{1a}$ and $TXB_2$ are stable metabolites of $PGI_2$ and thromboxane $A_2$ which have been implicated in increased risk for stroke and heart attack. HODEs are lipoxygenase-derived fatty acid metabolites.

DETAILED DESCRIPTION OF THE INVENTION

Introduction

Figure 1:
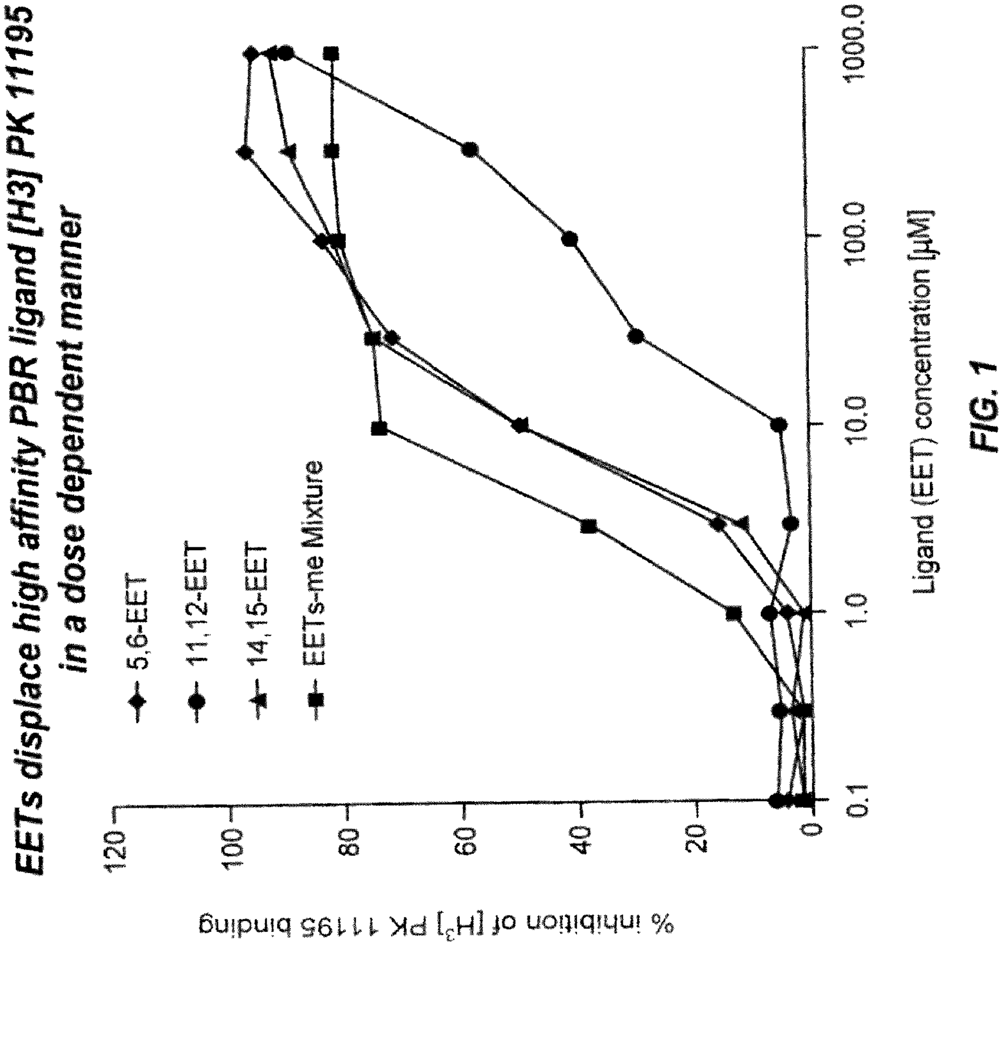
FIG. 1 is a graph showing the results of in vitro assays showing that EETs displace the high affinity PBR ligand [$H^3$] PK 11195 in a dose dependent manner. X axis: Micromolar concentration of EETs. Y axis: % Inhibition of binding of [$H^3$] PK 11195. Filled diamonds: 5,6-EET. Filled circles: 11,12-EET. Filled triangles: 14,15-EET. Filled squares: Mixture of epoxyeicosatrienoic acid methylesters (“EETs-me”).

The enzyme "soluble epoxide hydrolase" ("sEH") acts on an important branch of the arachidonic acid pathway degrading anti-inflammatory and analgesic metabolites. cis-Epoxyeicosatrienoic acids" ("EETs") are biomediators synthesized by cytochrome P450 epoxygenases, and are hydrolyzed by sEH into the corresponding diols, which are pro-inflammatory.

Surprisingly, it has now been discovered that EETs bind to the cannabinoid $CB_2$ receptor, peripheral benzodiazepine receptor ("PBR"), neurokinin $NK_2$ receptor, and dopamine $D_3$ receptor. The binding data alone did not, however, reveal whether EETs acted as agonists or antagonists of the biological functions of the receptors or would block endogenous ligands of the receptors from reaching them, thereby preventing normal activation or antagonism of the receptors.

Surprisingly, the in vivo studies reported herein show that EETs act as agonists for PBR and for $CB_2$ receptors. Further, the in vitro competitive binding assays reported herein show that EETs displace known high affinity ligands of the PBR and $CB_2$.

The findings reported herein show the pharmacological effect of increasing EETs in activating PBR activity. Persons of skill will therefore appreciate that sEHIs, which are known to result in increased levels of EETs, and EETs themselves, will activate PBR activity when administered, and are therefore useful for treating conditions in which modulating (and specifically, increasing) the activity of PBR reduces or eliminates symptoms. Similarly, the assays reported herein show the pharmacological effect of increasing EETs in activating $CB_2$ activity. Persons of skill will therefore appreciate and expect that sEHIs, which are known to result in increased levels of EETs, and EETs themselves, will activate $CB_2$ activity when administered, and are therefore useful for treating conditions in which increasing $CB_2$ activity reduces or eliminates symptoms.

The recognition that EETs binds to these molecular receptors permits the use of EETs (and analogs of EETs that are not susceptible or are less susceptible to hydrolysis by sEH) to address conditions for which it was not previously known EETs could be used. Further, since the administration of inhibitors of sEH increases the levels of EETs present in the body, inhibitors of sEH can also be administered, alone or in combination with EETs, to increase EETs levels and therefore to address these conditions (for convenience, inhibitors of sEH are sometimes alternatively referred to herein as "sEHI").

A selective $CB_2$ agonist has been shown to prevent the growth of glioma through a $CB_2$ dependant mechanism. In addition $CB_2$ receptors are known to modulate peripheral nociceptive transmission. Further, a relationship between cell proliferation and PBR expression has been observed in human astrocytomas and breast cancer cell lines and PBR expression is upregulated in many types of cancer. Similarly, PBR ligands induce in vitro inhibition of cancer cell proliferation and modulate steroidogenesis. The activation of PBR receptors reduces proliferation through several mechanisms, such as that described Carrier et al., *Inhibition of an equilibrative nucleoside transporter by cannabidiol: A mechanism of cannabinoid immunosuppression*, Proc Natl Acad Sci, 103: 7895-7900 (2006). Further, PBR ligands combined with cytotoxic agents have an anti-tumor effect in in vivo models. Since the studies reported herein reveal that EETs are agonists of both the PBR and the CB2 receptors, it is expected that they will work through both mechanisms to slow or prevent proliferation of glioma, astrocytoma and breast cancer cells, as well as other cancer cell types in which PBR expression is upregulated. Accordingly, administration of EETs, inhibitors of sEH, or both, can be administered to reduce the rate of growth of glioma cells, astrocytoma cells, and breast cancer cells, and other malignant tumor cells expressing PBR, and especially those in which PBR expression is upregulated.

Further, agonists of PBR are known to act as anxiolytics. This is presumably because of their ability to increase the acute synthesis of neurosteroids such as allopregnenolone. sEHI and EETs are therefore expected to act as anxiolytics to reduce symptoms of anxiety. Without wishing to be bound by theory, this is expected to be through modulating the endogenous neurosteroid tone. Since administration of inhibitors of sEH to an individual increases the level of EETs in the individual available to bind to the PBR during the period the inhibitor is present and active in the individual, inhibitors of sEH are also expected to act as anxiolytics. Additionally, EETs, inhibitors of sEH, or both should be useful for other indications in which anxiolytics are useful, including as a premedication for inducing sedation, anxiolysis or amnesia prior to certain medical procedures (e.g. endoscopy), as a means for reducing panic attacks, and states of agitation, as a treatment for status epilepticus, as adjunctive treatment of other forms of epilepsy, for reducing symptoms of alcohol and opiate withdrawal, for reducing insomnia, and for initial management of mania, together with first line drugs like lithium, valproate or other antipsychotics.

Since peripheral benzodiazepine receptors affect the rate of steroidogenesis, EETs or sEHI, or both, can be administered to affect the rate of steroidogenesis. In particular, EETs, or sEHI, or both, can be administered to reduce serum cholesterol levels. The EETs or sEHI, or both, can be used alone or in conjunction with one or more statins to augment the effect of the statin or statins.

Peripheral benzodiazepine receptors can also be targeted by EETs to protect cells against oxygen radical damage. PER ligands are known to decrease UV damage to cells and tissues. Accordingly, it is expected that inhibitors of sEHI and EETs can be administered to reduce UV damage and oxygen radical damage to cells. In some embodiments, EETs or inhibitors of sEH are administered systemically to protect cells against oxygen radical damage. Persons of skill are well aware of the potential for skin damage posed by prolonged exposure of skin to sunlight. In some embodiments, EETs or inhibitors of sEH are administered topically, for example by being mixed into a lotion, cream or other base suitable for topical administration, to reduce UV damage in skin exposed to sunlight. Conveniently, the cream or other base suitable for topical administration also contains a sunscreen or sunblock, such as oxybenzone, avobenzone, a cinnamate, octyl methoxycinnamate (OMC), ethylhexyl p-methoxycinnamate, a salicylate, octyl salicytate (OCS), para-aminobenzoic acid (PABA), padimate-O, octyl dimethyl paba, octocrylene, zinc oxide, titanium dioxide, benzophenone, or benzophenone-3. Sunscreens and sunblocks typically work by physically blocking or absorbing UV radiation whereas, as noted, EETs and inhibitors of sEH reduce UV damage. The two methods of protecting skin are therefore complementary and the combination of the two types of agent is expected to have at least additive, and possibly synergistic, effects in protecting skin. For example, EETs, inhibitors of sEH, or both can be administered to reduce the effect of photo-aging (aging of skin because of UV damage) and to reduce the likelihood of developing skin cancer due to repeated exposure to UV light. Since exposure to ionizing radiation is also believed to result in part from damage by oxygen radicals, EETs, inhibitors of sEH, or both, can be used topically on persons undergoing radiation therapy, particularly of the head and neck, to reduce incidental damage to the skin during the exposure to the radiation.

Neurokinin A ("NKA") and its receptor $NK_2$ have a known role in modulating gastric motility. In contrast to the PBR and $CB_2$ receptors, however, where it is activation of the receptor that results in alleviating symptoms of the conditions listed above, for the NK2 receptor it is reducing the activity of the receptor that is associated with alleviating symptoms therapeutically useful. For example, an antagonist of NKA activity is currently in Phase II clinical trials for irritable bowel syndrome ("IBS"), and the relationship between the activation of the $NK_2$ receptor and symptoms of IBS is well established in the art. The studies reported herein show that EETs displace ligands from the $NK_2$ receptor. The ability of EETs to displace endogenous ligands that would otherwise activate the receptor results in downregulating $NK_2$ receptor activity. Thus, EETs act as antagonists of endogenous $NK_2$ ligands and can be used to reduce symptoms of conditions that result from or are aggravated by, $NK_2$ receptor activation, including IBS. The administration of EETs or sEHI, or both, to persons suffering from IBS is therefore expected to reduce those symptoms.

The studies in the Examples report the results of both in vitro and in vivo assays. First, as shown in FIG. 1, an in vitro assay using the high affinity PBR ligand PK 11195 1-(2-Chlorophenyl-N-methylpropyl)-3-isoquinolinecarboxamide, a powerful PBR ligand. (See, Langer and Arbilla, Fund Clin Pharmacol 2(3):159-70 (1988)). The 5,6, 11,12, and 14,15 EETs all showed the ability to completely inhibit the binding of PK11195 at millimolar concentrations, while an EETs-me mixture inhibited PK11195 binding at millimolar concentrations in a dose-dependent manner, while a mixture of EETs-methylesters inhibited PK11195 binding more potently than any individual EET. The Kd of PK 11195 is 2.7 nM, while EETs displaced this high affinity ligand with an $IC_{50}$ of 4.6 μM for the EET me mixture.

The in vitro assays showed that EETs bind to PBR, but not whether EETs act as agonists or as antagonists of the receptor, or simply block the binding of other ligands which may have one of these activities. To determine what effect, if any, EETs have on the PBR, in vivo assays were performed. It is known that peripheral benzodiazepine receptors affect the rate of steroidogenesis. We have previously found that inhibitors of sEH have an effect as analgesics using a well accepted animal model for measuring analgesia. We hypothesized that sEHI-elicited analgesia was induced through action on the PBR, and realized we could determine whether determine whether EETs acted as an agonist of PBR, as an antagonist, or as neither, by co-administering inhibitors of sEH and compounds that are inhibitors of steroid synthesis and seeing if they blocked sEH-elicited analgesia. Steroid synthesis inhibitors have previously been shown to be antagonists of PBR. See, e.g., Papadopoulos, et al., *Peripheral-type benzodiazepine receptor in neurosteroid biosynthesis, neuropathology and neurological disorders*, Neuroscience (138), p 749-756 (2006) and da Silva et al., *Involvement of steroids in anti-inflammatory effects of PK*11195 *in a murine model of pleurisy*. Mediators of Inflammation (13), p 93-103 (2004).

Figures 2A, 2B, 2C, 2D:
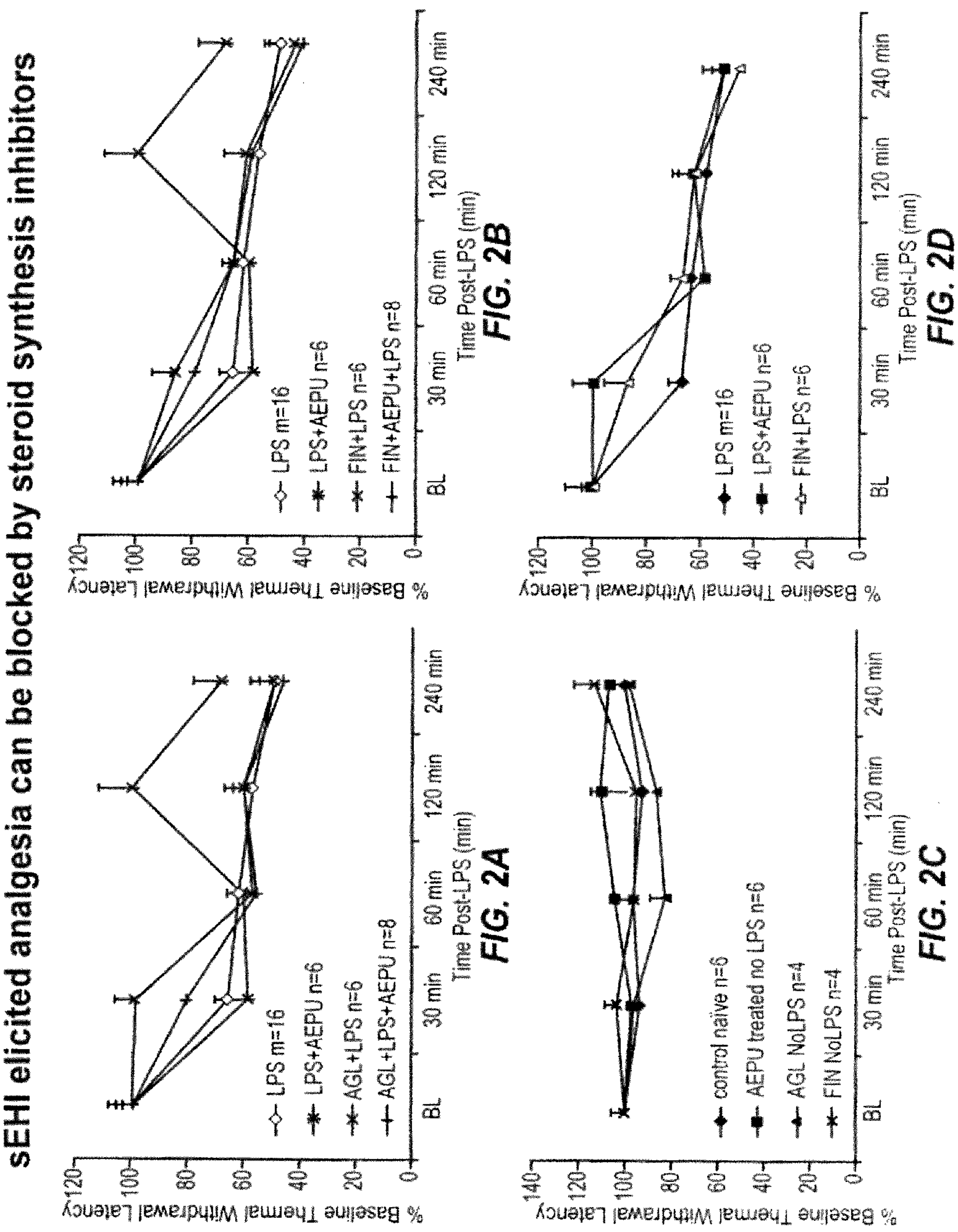
FIGS. 2A-2D show the results of in vivo assays showing that sEHI elicited analgesia in rats can be blocked by steroid synthesis inhibitors.
Figure 4:
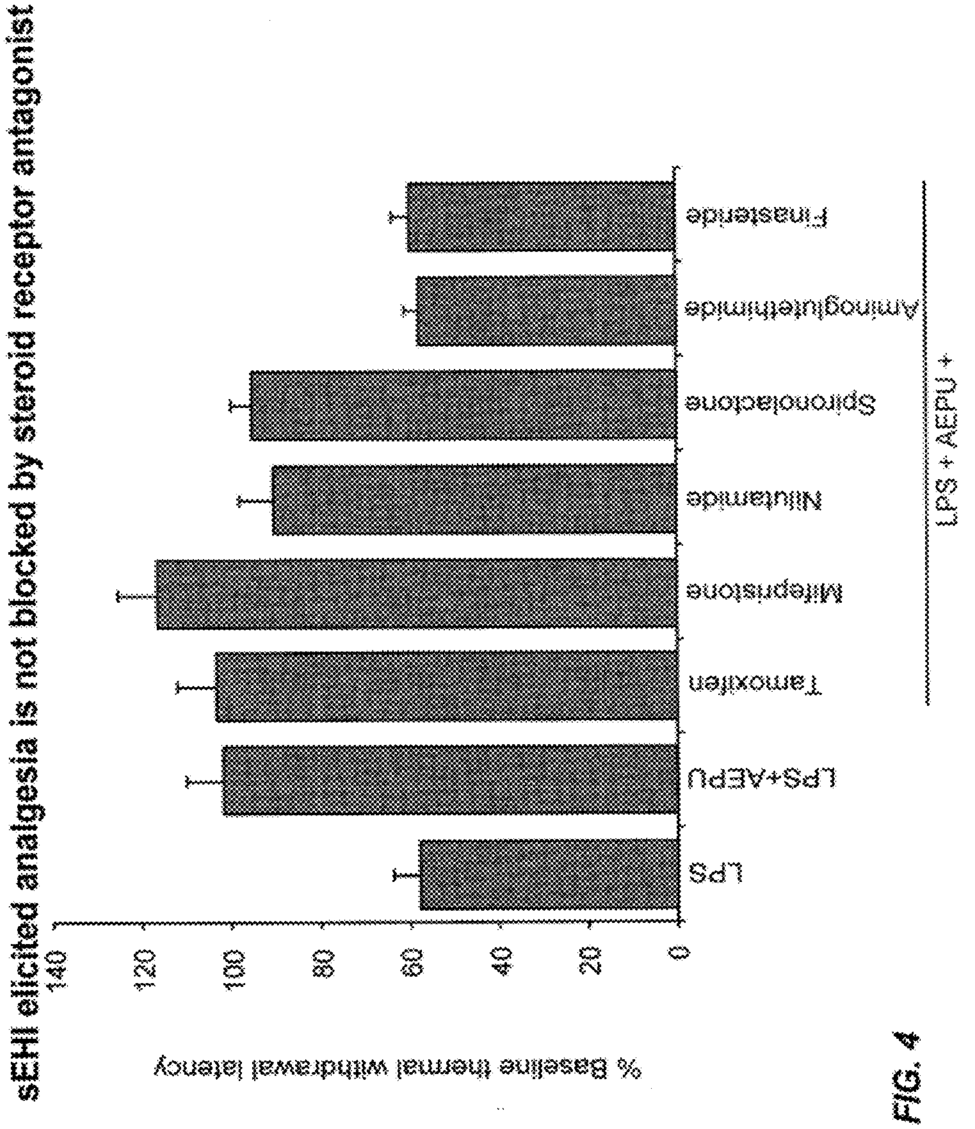
FIG. 4 is a graph of in vivo data showing that analgesia induced by the action of sEH inhibitors is not blocked by steroid receptor antagonists. The Y axis shows hindpaw thermal withdrawal latencies ("TWL") as a percentage of TWL prior to any treatment ("Baseline"). The bars on X axis shows the result of testing using the agent or agents listed below the bar. LPS: lipopolysaccharide. AEPU: sEH inhibitor. Tamoxifen is an estrogen receptor antagonist. Mifepristone is a glucocorticoid receptor antagonist. Nilutamide is an androgen receptor antagonist. Aminogluthethimide is a general steroid synthesis inhibitor. Finasteride is a 5 alpha reductase inhibitor that acts as a specific steroid synthesis inhibitor. The line at the bottom of the Figure under which is stated "LPS+AEPU+" indicates that the bars above that line reflect the results of studies in which the animals were treated with LPS, AEPU, and the antagonist listed over the line.

In vivo assays were conducted using two different inhibitors of steroid synthesis. The steroid synthesis inhibitor aminogluthetimide (AGL), effectively blocks all steroid synthesis by inhibiting the first enzyme, P450scc, in the steroid synthesis pathway. When topically administered to rats, AGL completely blocked the antihyperalgesic action of the sEHI AEPU in the LPS-elicited inflammatory pain model. See, FIG. 2A. Additionally, another inhibitor, finasteride, blocks 5a reductase and stops the steroid biosynthesis by blocking the conversion of testosterone to dihydrotestosterone in case of steroids and the conversion of progesterone to allopregnanolone in case of neurosteroids. Finasteride also blocked the anti-hyperalgesic activity of AEPU. See, FIG. 2B. In contrast, however, in vivo assays employing a non-steroidal estrogen receptor antagonist, tamoxifen, a dual progesterone/glucocorticoid receptor antagonist, mifepristone, an androgen receptor antagonist, nilutamide, and an aldosterone receptor antagonist, spironoloactone, showed that these antagonists did not have any impact on the antihyperalgesic action of AEPU, indicating that sEHIs and/or EETs do not act through these steroid receptors. See, FIG. 4.

Figure 5:
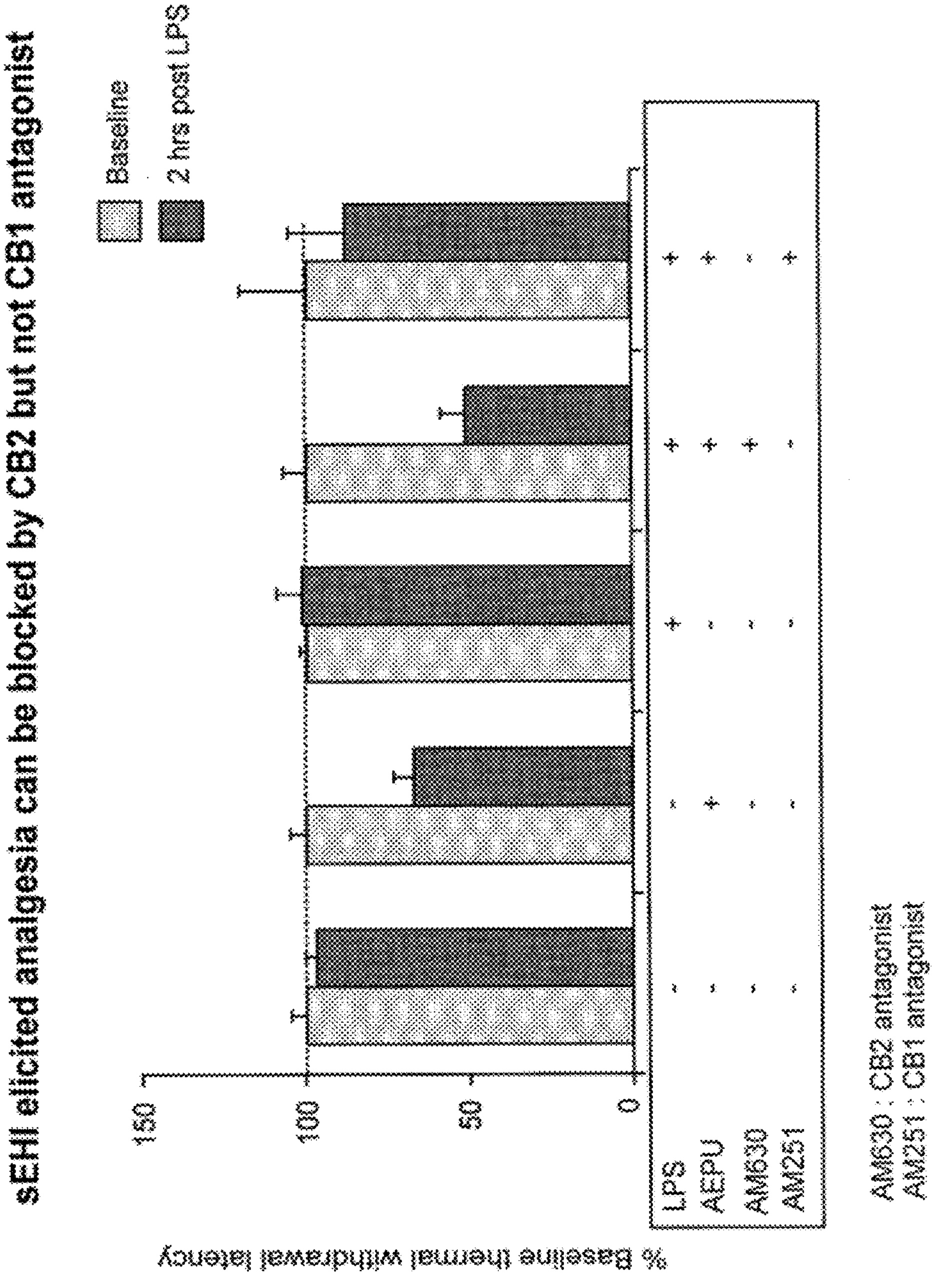
FIG. 5 is a graph of in vivo data showing that analgesia induced by the action of sEH inhibitors is blocked by an antagonist of the cannabinoid receptor $CB_2$, but not by an antagonist of the cannabinoid receptor $CB_1$. The Y axis shows hindpaw thermal withdrawal latencies ("TWL") as a percentage of TWL prior to any treatment ("Baseline"). The bars on X axis shows the result of testing using the agent or agents listed below the bar at Baseline and two hours post administration of lipopolysaccharide ("LPS"). 950: sEH inhibitor compound 950. AM630: iodopravadoline, a $CB_2$ antagonist. AM251: N-(piperidin-1-yl)-5-(4-iodophenyl)-1-(2,4-dichlorophenyl)-4-methy 1-1H-pyrazole-3-carboxamide, a $CB_1$ antagonist. +sign: shows experiment in which agent on corresponding horizontal line is present. −sign: shows experiment in which agent on corresponding horizontal line is absent. Line above bar shows error range. First pair of bars shows control experiment in which LPS is not administered.

In vivo assays were also conducted to determine whether EETs act to activate or to antagonize $CB_2$ receptor activity. We performed in vivo assays using antagonists of both $CB_1$ and $CB_2$, essentially blocking the activity of these receptors, to determine the contribution of cannabinoid receptor activation to sEHI attained analgesia. As shown in FIG. 5, a $CB_1$ antagonist, AM251 (N-(piperidin-1-yl)-5-(4-iodophenyl)-1-(2,4-dichlorophenyl)-4-methy 1-1H-pyrazole-3-carboxamide, see, e.g., Gatley et al., Eur J Pharmacol 1996 Jul. 4; 307(3):331-8 (1996)) did not block sEHI-elicited analgesia, whereas a $CB_2$ antagonist, AM630 (iodopravadoline, an aminoalkylindole, see, e.g., Pertwee et al., Life Sci. 56(23-24): 1949-55 (1995)) completely blocked sEHI-elicited analgesia. These assays established that if $CB_2$ receptors are blocked by a selective $CB_2$ antagonist such as AM630, sEHIs can not elicit analgesia and that $CB_2$ receptor activation is required for the analgesic activity of sEHIs. In contrast, elimination of the activity of $CB_1$ receptors had no impact on the analgesic activity of sEHIs.

Medicaments of EETs can be made which can be administered by themselves or in conjunction with one or more sEH inhibitors, or a medicament containing one or more sEH inhibitors can optionally contain one or more EETs. The EETs can be administered alone, or concurrently with a sEH inhibitor or following administration of a sEH inhibitor. It is understood that, like all drugs, sEH inhibitors have half lives defined by the rate at which they are metabolized by or excreted from the body, and that the sEH inhibitor will have a period following administration during which it will be present in amounts sufficient to be effective. If EETs administered after an sEH inhibitor are intended to be administered while the sEH inhibition is still in effect, therefore, it is desirable that the EETs be administered during the period during which the inhibitor will be present in amounts to be effective to delay hydrolysis of the EETs. Typically, in such a situation, the EET or EETs will be administered within 48 hours of administering an sEH inhibitor. More preferably, where the effect of the EET or EETs is intended to be enhanced by the effect of an sEHI, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor. In some embodiments, the person being treated with the EET or EETs does not have one of the disorders listed above as a condition which the subject being treated with an sEHI does not have. In some embodiments, the person being treated with the EET or EETs is not being treated for atherosclerosis, other inflammatory conditions, or other conditions in which inhibition of adhesion molecule expression, particularly on endothelial cells, is desirable.

In some embodiments, the sEH inhibitor may be a nucleic acid, such as a small interfering RNA (siRNA) or a micro RNA (miRNA), which reduces expression of a gene encoding sEH. Optionally, EETs may be administered in combination with such a nucleic acid. Typically, a study will determine the time following administration of the nucleic acid before a decrease is seen in levels of sEH. The EET or EETs are typically then administered at a time calculated to be after expression of the nucleic acid has resulted in a decrease in sEH levels.

Patients Who can Benefit from Use of EETs or sEHI or Both

In some embodiments of the invention, the person being treated with EETs, sEHI, or both, does not have hypertension or is not currently being treated with an anti-hypertension agent that is an inhibitor of sEH. In some embodiments, the person being treated does not have inflammation or, if he or she has inflammation, has not been treated with an sEH inhibitor as an anti-inflammatory agent. In some preferred embodiments, the person is being treated for inflammation but by an anti-inflammatory agent, such as a steroid, that is not an inhibitor of sEH. Whether or not any particular anti-inflammatory or anti-hypertensive agent is also an sEH inhibitor can be readily determined by standard assays, such as those taught in U.S. Pat. No. 5,955,496.

In some embodiments, the patient's disease or condition is not caused by an autoimmune disease or a disorder associated with a T-lymphocyte mediated immune function autoimmune response. In some embodiments, the patient does not have a pathological condition selected from type 1 or type 2 diabetes, insulin resistance syndrome, atherosclerosis, coronary artery disease, angina, ischemia, ischemic stroke, Raynaud's disease, or renal disease. In some embodiments, the patient is not a person with diabetes mellitus whose blood pressure is 130/80 or less, a person with metabolic syndrome whose blood pressure is less than 130/85, a person with a triglyceride level over 215 mg/dL, or a person with a cholesterol level over 200 mg/dL or is a person with one or more of these conditions who is not taking an inhibitor of sEH. In some embodiments, the patient does not have an obstructive pulmonary disease, an interstitial lung disease, or asthma. In some embodiments, the patient is not also currently being treated with an inhibitor of one or more enzymes selected from the group consisting of cyclo-oxygenase ("COX")-1, COX-2, and 5-lipoxygenase ("5-LOX"), or 5-lipoxygenase activating protein ("FLAP"). It is noted that many people take a daily low dose of aspirin (e.g., 81 mg) to reduce their chance of heart attack, or take an occasional aspirin to relieve a headache. It is not contemplated that persons taking low dose aspirin to reduce the risk of heart attack would ordinarily take that aspirin in combination with an EET or sEHI to potentiate that effect. It is also not contemplated that persons taking an occasional aspirin or ibuprofen tablet to relieve a headache or other episodic minor aches or pain would ordinarily take that tablet in combination with an EET or sEHI to potentiate that pain relief, as opposed to persons seeking relief for chronic pain from arthritis or other conditions requiring significant pain relief over an extended period. In some embodiments, therefore, the patient being treated by the methods of the invention may have taken an inhibitor of COX-1, COX-2, or 5-LOX in low doses, or taken such an inhibitor on an occasional basis to relieve an occasional minor ache or pain. In some embodiments, the patient does not have dilated cardiomyopathy or arrhythmia. In some embodiments, the patient is not using EETs or sEHI topically for pain relief. In some embodiments, the patient is not administering EETs or sEHI topically to the eye to relieve, for example, dry eye syndrome or intraocular pressure. In some embodiments, the patient does not have glaucoma or is being treated for glaucoma with agents that do not also inhibit sEH.

Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases. As discussed further in a separate section below, while the use of unmodified EETs is the most preferred, derivatives of EETs, such as amides and esters (both natural and synthetic), EETs analogs, and EETs optical isomers can all be used in the methods of the invention, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides. The addition of water to the epoxides results in the corresponding 1,2-diols (Hammock, B. D. et al., in Comprehensive Toxicology Biotransformation (Elsevier, New York), pp. 283-305 (1997); Oesch, F. Xenobiotica 3:305-340 (1972)). Four principal EH's are known: leukotriene epoxide hydrolase, cholesterol epoxide hydrolase, microsomal EH ("mEH"), and soluble EH ("sEH," previously called cytosolic EH). The leukotriene EH acts on leukotriene A4, whereas the cholesterol EH hydrates compounds related to the 5,6-epoxide of cholesterol. The microsomal epoxide hydrolase metabolizes monosubstituted, 1,1-disubstituted, cis-1,2-disubstituted epoxides and epoxides on cyclic systems to their corresponding diols. Because of its broad substrate specificity, this enzyme is thought to play a significant role in ameliorating epoxide toxicity. Reactions of detoxification typically decrease the hydrophobicity of a compound, resulting in a more polar and thereby excretable substance.

"Soluble epoxide hydrolase" ("sEH") is an epoxide hydrolase which in many cell types converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1): 61-71 (1995). Soluble epoxide hydrolase represents a single highly conserved gene product with over 90% homology between rodent and human (Arand et al., FEBS Lett., 338: 251-256 (1994)). Soluble EH is only very distantly related to mEH and hydrates a wide range of epoxides not on cyclic systems. In contrast to the role played in the degradation of potential toxic epoxides by mEH, sEH is believed to play a role in the formation or degradation of endogenous chemical mediators. Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

Neurokinin Receptors

Neurokinins are a family of regulatory peptides that are widely distributed throughout the mammalian body where they are known to act as neurotransmitters in both the central and peripheral nervous systems. In the periphery, neurokinin receptors are mostly found in capsaicin-sensitive sensory nerves, which are now accepted not only to relay information to the central nervous system, but also to release peptide neurotransmitters from the efferent terminals; this release can bring about effects in surrounding tissues. The mammalian tachykinins include substance P(SP), neurokinin A (NKA)

and neurokinin B (NKB) which preferentially act at three G-protein-linked receptors termed $NK_1$, $NK_2$ and $NK_3$ respectively, though at high concentrations they can act at all three receptors. Activation, of the neurokinin receptors can lead to a wide variety of biological actions such as smooth muscle contraction, vasodilation, secretion, neurogenic inflammation and activation of the immune system. One of the known roles of NKA and its receptor $NK_2$ is in modulating gastric motility. The Neurokinin $NK_2$ receptor is being targeted by several pharmaceutical companies for treatment of gastrointestinal disorders. For example, the Menarini Group (Florence, Italy) has a $NK_2$ antagonist, Nepadutant (a glycosylated bicyclic peptide) in Phase II clinical trials for bronchial hyperactivity and irritable bowel syndrome (IBS). Hyperalgesia is due to sensitization of sensory receptors or nociceptors. Visceral hyperalgesia has been recognized as the main pathophysiological event underlying IBS symptoms. The proposed mechanism of action of this compound is that in animal models of IBS it corrects colon visceral hyperalgesia.

Cannabinoid Receptors

Cannabinoids, the active components of *Cannabis saliva*, and their derivatives, exert a wide spectrum of central and peripheral actions, such as analgesia, anticonvulsion, anti-inflammation, and alleviation of both intraocular pressure and emesis. Two different cannabinoid receptors have been characterized and cloned from mammalian tissues, $CB_1$ and $CB_2$. $CB_1$ is expressed primarily in the central nervous system, whereas $CB_2$ is expressed primarily in cells of the immune system and is absent in neurons of the central nervous system. Cannabinoid agonists suppress nociceptive transmission and inhibit pain-related behavior in animal models of acute and persistent nociception. $CB_2$-selective agonists fail to elicit centrally mediated cannabimimetic effects such as hypothermia, catalepsy, and hypoactivity and are unlikely to be psychoactive or addictive. Activation of $CB_2$ on non-neuronal cells in inflamed tissue is postulated to suppress the release of inflammatory mediators implicated in nociceptor sensitization. The recent development of selective agonists and antagonists for $CB_2$ has provided the pharmacological tools necessary to evaluate the role of CB2 in modulating persistent nociception. $CB_2$-selective agonists have recently been shown to induce antinociception in models of acute, inflammatory, and nerve injury-induced nociception. AM1241, a $CB_2$-selective agonist, exhibits 340-fold selectivity for $CB_2$ over $CB_1$. AM1241 also attenuates neuropathic pain through a $CB_2$ mechanism that is not dependent upon $CB_1$. Another selective $CB_2$ agonist JWH-133 prevents the growth of glioma through a $CB_2$ dependant mechanism.

Peripheral Benzodiazepine Receptors

Two main functions of peripheral benzodiazepine receptors ("PBR") have been described: a role in steroidogenesis and modulation of the apoptotic process. With respect to steroidogenesis, PBR bind cholesterol and mediates its transport from the outer to the inner mitochondrial membranes. This translocation is the first and rate limiting step for steroid synthesis. PBR activation results in an increase in pregnenolone formation and the synthesis of downstream steroids. PBR are also involved in human cancer cell proliferation. A relationship between cell proliferation and PBR expression has been observed in human astrocytomas and breast cancer cell lines. Similarly, PBR ligands induce in vitro inhibition of cancer cell proliferation.

Turning to apoptosis, apoptosis (also referred to as "programmed cell death") is mainly under the control of mitochondria; and the mitochondrial permeability transition pore plays a key role in this regulation. Mitochondrial membrane permeabilization ("MMP") therefore is a major check-point in the cascade of biochemical events leading to the induction of programmed cell death. A number of apoptosis-inducing signals induce MMP and anti-apoptotic proteins block this alteration. The loss of mitochondrial membrane integrity leads to a drop of transmembrane potential and remodeling of mitochondrial ultra-structure that allow the release of toxic intermembrane proteins into the cytoplasm such as cytochrome c. These apoptotic effectors are then responsible for the late events of the cell death process. The PTP therefore appears to be a multiprotein complex whose molecular dynamics could be influenced by several partners. PBR is one of these partners and can therefore be used as a target in clinical and therapeutic approaches. Numerous observations indicate that PBR participates in the regulation of apoptosis: (i) transfection-enforced overexpression of PBR attenuates apoptosis induced by oxygen radicals or ultraviolet light, (ii) permeabilized mitochondria release DBI that binds intact mitochondria and accelerates MMP induction throughout the cell, (iii) the myxoma poxvirus M11L protein inhibits host cell apoptosis via a physical and functional interaction with PBR, and (iv) various PBR ligands with nanomolar affinity for the receptor, such as Ro-4864 and PK11195, modulate cancer cell response to apoptosis-inducing signals. PBR ligand-induced enhancement of apoptosis clearly acts via mitochondrial targeting. PBR ligands combined with cytotoxic agents have an anti-tumor effect in in vivo models.

There is also evidence for a role played by PBR in regulation of inflammation processes, as various in vivo mouse models of acute inflammation have shown that PBR ligands inhibit inflammatory signs of pleurisy, arthritis or lupus erythematosus. These effects are thought to occur through (i) modulation of the human natural killer cell activity, (ii) induction of heat shock protein expression, (iii) modulation of the activity of monocytes/macrophages and (iv) restoration of the apoptotic process in auto-immune components. Other functions of PBR include regulation of ischemia-reperfusion injury via membrane biogenesis, protection of hematopoietic cells against oxygen radical damage, lipid fluidity of mitochondria, modulation of bronchomotor tone, erythroid differentiation, intracellular transport of heme and porphyrins.

Irritable Bowel Syndrome

Irritable bowel syndrome, or IBS, is considered one of the most common reasons people see their doctor in the U.S., accounting for more than one out of every 10 doctor visits. According to the National Digestive Diseases Information Clearinghouse, of the National Institute of Diabetes and Digestive and Kidney Diseases (NIDDK), IBS is a functional disorder that affects mainly the bowel. IBS is characterized by over-sensitivity of the nerves and muscles of the bowel, which typically results in cramping, bloating, gas, diarrhea, and constipation. In persons with IBS, symptoms can be triggered by stress, exercise, and hormones, as well as by foods such as milk products, chocolate, alcohol, caffeine, carbonated drinks, and fatty foods. Since there is no cure, patients with IBS are usually treated to relieve symptoms, by diet changes, medicine such as anti-spasmotics to slow bowel contractions, and stress relief. One medication, alosetron (5-methyl-2-[(4-methyl-1H-imidazol-5-yl)methyl]-3,4-dihydro-2H-pyrido [4,3-b]indol-1 (5H)-one), a 5-$HT_4$ antagonist used to block serotonin activity in the intestinal tract, is currently only approved for use in women with IBS in which diarrhea predominates, but its use is sharply limited due to potentially serious side effects on the gastrointestinal tract. A second, tegaserod (1-{[5-(hydroxymethyl)-1H-indol-3-yl]methylideneamino}-2-pentyl-guanidine) is also a serotonin type 4 receptor ("5-$HT_4$") partial agonist and is approved for short-term use in women with IBS. Since EETs bind to a different receptor than do alosetron and tegaserod, the problems associated with the use of these agents, and with alosetron in particular, are not expected with the uses and methods of the present invention.

Inhibitors of Soluble Epoxide Hydrolase

Scores of sEH inhibitors are known, of a variety of chemical structures. Derivatives in which the urea, carbamate, or amide pharmacophore (as used herein, "pharmacophore" refers to the section of the structure of a ligand that binds to the sEH) is covalently bound to both an adamantane and to a 12 carbon chain dodecane are particularly useful as sEH inhibitors. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S. A, 96:8849-8854 (1999), which provides substantial guidance on designing urea derivatives that inhibit the enzyme.

Derivatives of urea are transition state mimetics that form a preferred group of sEH inhibitors. Within this group, N,N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH.) Thus, isomers of adamantyl dodecyl urea are preferred inhibitors. It is further expected that N,N'-dodecyl-cyclohexyl urea (DCU), and other inhibitors of sEH, and particularly dodecanoic acid ester derivatives of urea, are suitable for use in the methods of the invention. Preferred inhibitors include:

2-(3-Adamantan-1-yl-ureido)dodecanoic acid (AUDA),

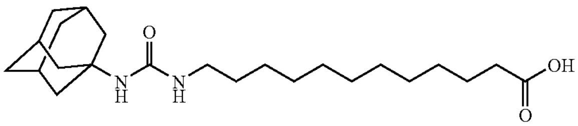

12-(3-Adamantan-1-yl-ureido)dodecanoic acid butyl ester (AUDA-BE),

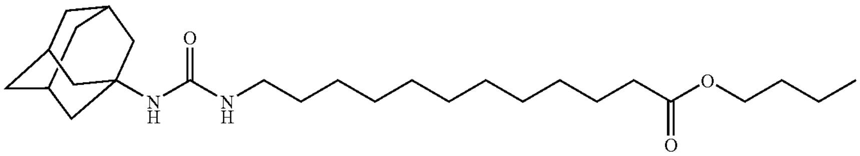

Adamantan-1-yl-3-{5-[2-(2-ethoxyethoxy)ethoxy]pentyl}urea (compound 950, also referred to herein as "AEPU"), and

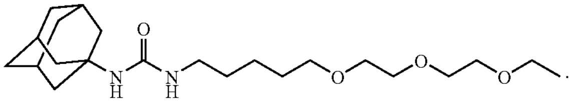.

Another preferred group of inhibitors are piperidines. The following Table sets forth some exemplar piperidines and their ability to inhibit sEH activity, expressed as the amount needed to reduce the activity of the enzyme by 50% (expressed as "$IC_{50}$").

TABLE 1

$IC_{50}$ values for selected alkylpiperidine-based sEH inhibitors

| | | n = 0 | | n = 0 | |
|---|---|---|---|---|---|
| 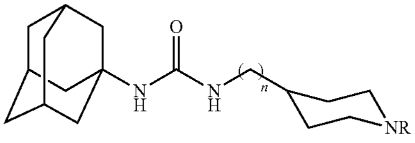 | | Compound | $IC_{50}$ (μM)[a] | Compound | $IC_{50}$ (μM)[a] |
| R: | H | I | 0.30 | II | 4.2 |
| | 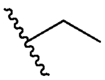 | 3a | 3.8 | 4.a | 3.9 |

TABLE 1-continued

IC$_{50}$ values for selected alkylpiperidine-based sEH inhibitors

| 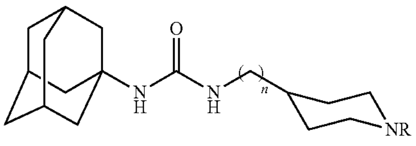 | n = 0 | | n = 0 | |
|---|---|---|---|---|
| | Compound | IC$_{50}$ (μM)[a] | Compound | IC$_{50}$ (μM)[a] |
| 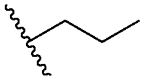 | 3b | 0.81 | 4b | 2.6 |
| 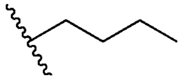 | 3c | 1.2 | 4c | 0.61 |
| 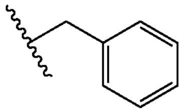 | 3d | 0.01 | 4d | 0.11 |

[a]As determined via a kinetic fluorescent assay.

A number of other sEH inhibitors which can be used in the methods and compositions of the invention are set forth in co-owned applications PCT/US2004/010298 and U.S. Published Patent Application Publication 2005/0026844.

U.S. Pat. No. 5,955,496 (the '496 patent) also sets forth a number of sEH inhibitors which can be use in the methods of the invention. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenyl chalcone oxide and 4-fluourochalcone oxide. The phenyl glycidols and chalcone oxides are believed to form stable acyl enzymes.

Additional inhibitors of sEH suitable for use in the methods of the invention are set forth in U.S. Pat. Nos. 6,150,415 (the '415 patent) and 6,531,506 (the '506 patent). Two preferred classes of inhibitors of the invention are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty inhibitors of Formula 2, which were shown to inhibit human sEH at concentrations as low as 0.1 μM. Any particular inhibitor can readily be tested to determine whether it will work in the methods of the invention by standard assays. Esters and salts of the various compounds discussed above or in the cited patents, for example, can be readily tested by these assays for their use in the methods of the invention.

As noted above, chalcone oxides can serve as an alternate substrate for the enzyme. While chalcone oxides have half lives which depend in part on the particular structure, as a group the chalcone oxides tend to have relatively short half lives (a drug's half life is usually defined as the time for the concentration of the drug to drop to half its original value. See, e.g., Thomas, G., Medicinal Chemistry: an introduction, John Wiley & Sons Ltd. (West Sussex, England, 2000)). Since the various uses of the invention contemplate inhibition of sEH over differing periods of time which can be measured in days, weeks, or months, chalcone oxides, and other inhibitors which have a half life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half lives although, for inhibitors with a relatively short half life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors of the invention mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

Preferably, the inhibitor inhibits sEH without also significantly inhibiting microsomal epoxide hydrolase ("mEH"). Preferably, at concentrations of 500 μM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 500 μM. Inhibitors with $IC_{50}$s of less than 500 μM are preferred, with $IC_{50}$s of less than 100 μM being more preferred and, in order of increasing preference, an $IC_{50}$ of 50 μM, 40 μM, 30 μM, 25 μM, 20 μM, 15 μM, 10 μM, 5 μM, 3 μM, 2 μM, 1 μM or even less being still more preferred. Assays for determining sEH activity are known in the art and described elsewhere herein.

EETs

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. For example, in one prior report of EETs administration, EETs were administered by catheters inserted into mouse aortas. The EETs were infused continuously during the course of the experiment because of concerns over the short half life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

In studies from the laboratory of the present inventors, however, it has been shown that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be administered without also administering an sEHI to provide a therapeutic effect. Moreover, we have found that EETs, if not exposed to acidic conditions or to sEH are stable and can withstand reasonable storage, handling and administration.

In short, sEHI, EETs, or co-administration of sEHIs and of EETs, can be used in the methods of the present invention. In some embodiments, one or more EETs are administered to the patient without also administering an sEHI. In some embodiments, one or more EETs are administered shortly before or concurrently with administration of an sEH inhibitor to slow hydrolysis of the EET or EETs. In some embodiments, one or more EETs are administered after administration of an sEH inhibitor, but before the level of the sEHI has diminished below a level effective to slow the hydrolysis of the EETs.

EETs useful in the methods of the present invention include 14,15-LET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

If desired, EETs, analogs, or derivatives that retain activity can be used in place of or in combination with unmodified EETs. Liao and Zeldin, supra, define EET analogs as compounds with structural substitutions or alterations in an EET, and include structural analogs in which one or more EET olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, difluorocycloprane, or carbonyl, while in others, the carboxylic acid moiety is replaced with a commonly used mimic, such as a nitrogen heterocycle, a sulfonamide, or another polar functionality. In preferred forms, the analogs or derivatives are relatively stable as compared to an unmodified EET because they are more resistant than an unmodified EET to sEH and to chemical breakdown. “Relatively stable” means the rate of hydrolysis by sEH is at least 25% less than the hydrolysis of the unmodified EET in a hydrolysis assay, and more preferably 50% or more lower than the rate of hydrolysis of an unmodified EET. Liao and Zeldin show, for example, episulfide and sulfonamide EETs derivatives. Amide and ester derivatives of EETs and that are relatively stable are preferred embodiments. In preferred forms, the analogs or derivatives have the biological activity of the unmodified EET regioisomer from which it is modified or derived in binding to the CB2 or peripheral BZD receptor. Whether or not a particular EET analog or derivative has the biological activity of the unmodified EET can be readily determined by using it in standard assays, such as radio-ligand competition assays to measure binding to the relevant receptor. As mentioned in the Definition section, above, for convenience of reference, the term “EETs” as used herein refers to unmodified EETs, and EETs analogs and derivatives unless otherwise required by context.

In some embodiments, the EET or EETs are embedded or otherwise placed in a material that releases the EET over time. Materials suitable for promoting the slow release of compositions such as EETs are known in the art. Optionally, one or more sEH inhibitors may also be placed in the slow release material.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as “enteric coatings” are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name “Eudragit®”. The choice of the particular enteric coating is not critical to the practice of the invention.

Assay for Epoxide Hydrolase Activity

Any of a number of standard assays for determining epoxide hydrolase activity can be used to determine inhibition of sEH. For example, suitable assays are described in Gill, et al., Anal Biochem 131:273-282 (1983); and Borhan, et al., Analytical Biochemistry 231:188-200 (1995)). Suitable in vitro assays are described in Zeldin et al., J. Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rifling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174:291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous method of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

Other Means of Inhibiting sEH Activity

Other means of inhibiting sEH activity or gene expression can also be used in the methods of the invention. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

“RNA interference,” a form of post-transcriptional gene silencing (“PTGS”), describes effects that result from the introduction of double-stranded RNA into cells (reviewed in Fire, A. Trends Genet. 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as “sequence non-specific RNA interference,” characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2$\alpha$, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, “short interfering RNA” (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). The amino acid sequence of human sEH (SEQ ID NO:1) and the nucleotide sequence encoding that amino acid sequence (SEQ ID NO.:2) are set forth in U.S. Pat. No. 5,445,956.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research on the internet by entering “http://” followed by “jura.wi.mit.edu/pubint/http://iona.wi.mit.edu/siRNAext/.”

For example, using the program available from the Whitehead Institute, the following sEH target sequences and siRNA sequences can be generated:

```
1) Target: CAGTGTTCATTGGCCATGACTGG            (SEQ ID NO: 3)
Sense-siRNA: 5'-GUGUUCAUUGGCCAUGACUTT-3'      (SEQ ID NO: 4)
Antisense-siRNA: 5'-AGUCAUGGCCAAUGAACACTT-3'  (SEQ ID NO: 5)

2) Target: GAAAGGCTATGGAGAGTCATCTG            (SEQ ID NO: 6)
Sense-siRNA: 5'-AAGGCUAUGGAGAGUCAUCTT-3'      (SEQ ID NO: 7)
Antisense-siRNA: 5'-GAUGACUCUCCAUAGCCUUTT-3'  (SEQ ID NO: 8)

3) Target AAAGGCTATGGAGAGTCATCTGC             (SEQ ID NO: 9)
Sense-siRNA: 5'-AGGCUAUGGAGAGUCAUCUTT-3'      (SEQ ID NO: 10)
Antisense-sIRNA: 5'-AGAUGAGUGUCCAUAGCCUTT-3'  (SEQ ID NO: 11)

4) Target: CAAGCAGTGTTCATTGGCCATGA            (SEQ ID NO: 12)
Sense-siRNA: 5'-AGCAGUGUUCAUUGGCCAUTT-3'      (SEQ ID NO: 13
Antisense-siRNA: 5'-AUGGCCAAUGAACACUGCUTT-3'  (SEQ ID NO: 14

5) Target: CAGGACATGGAGGACTGGATTCC            (SEQ ID NO: 15)
Sense-siRNA: 5'-GCACAUGGAGGACUGGAUUTT-3'      (SEQ ID NO: 16)
Antisense-siRNA: 5'-AAUCCAGUCCUCCAUGUGCTT-3'  (SEQ ID NO: 17)
```

Alternatively, siRNA can be generated using kits which generate siRNA from the gene. For example, the “Dicer siRNA Generation” kit (catalog number T510001, Gene Therapy Systems, Inc., San Diego, Calif.) uses the recombinant human enzyme “dicer” in vitro to cleave long double stranded RNA into 22 by siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 by dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a “spacer”) to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

```
1) Target: CAGTGTTCATTGGCCATGACTGG                              (SEQ ID NO: 19)
Sense strand: 5'-GATGCCCGTGTTCATTGGCCATGACTTTCAA                (SEQ ID NO: 20)
GAGAAGTGATGGCCAATGAACACTTTTT-3'
Antisense strand: 5'-AGCTAAAAAGTGTTCATTGGCCATGACTTCTCTT         (SEQ ID NO: 21)
GAAAGTCATGGCCAATGAACACGGG-3'

2) Target: GAAAGGCTATGGAGAGTCATCTG                              (SEQ ID NO: 22)
Sense strand: 5'-GATCCCCAAGGCTATGGAGAGTCATCTTCAAGAGAGA          (SEQ ID NO: 23)
TGACTCTCCATAGCCTTTTTTT-3'
Antisense strand: 5'-AGCTAAAAAAAGGCTATGGAGAGTCATCTCTCTTGAA      (SEQ ID NO: 24)
GATGACTCTCCATAGCCTTGGG-3'

3) Target: AAAGGCTATGGAGAGTCATCTGC                             (SEQ ID NO: 25)
Sense strand: 5'-GATCCCCAGGCTATGGAGAGTCATCTTTCAAGAGAAG          (SEQ ID NO: 26)
ATGACTCTCCATAGCCTTTTTT-3'
Antisense strand: 5'-AGCTAAAAAAGGCTATGGAGAGTCATCATCTCTTG        (SEQ ID NO: 27)
AAAGATGACTCTCCATAGCCTGGG-3'

4) Target: CAAGCAGTGTTCATTGGCCATGA                             (SEQ ID NO: 28)
Sense strand: 5'-GATCCCCAGCAGTGTTCATTGGCCATTTCAAGAGAATG         (SEQ ID NO: 29)
GCCAATGAACACTGCTTTTTT-3'
Antisense strand: 5'-AGCTAAAAAAGCAGTGTTCATTGGCCATTCTCTTGAAATG   (SEQ ID NO: 30)
GCCAATGAACACTGCTGGG-3'

5) Target: CAGCACATGGAGGACTGGATTCC                             (SEQ ID NO: 31)
Sense strand 5'-GATCCCCGCACATGGAGGACTGGATTTTCAAGAGAAATC         (SEQ ID NO: 32)
CAGTCCTCCATGTGCTTTTT-3'
Antisense strand: 5'-AGCTAAAAAGCACATGGAGGACTGGATTTCTCTTGAAAA    (SEQ ID NO: 33)
TCCAGTCCTCCATGTGCGGG-3'
```

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264: 17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program on the internet which can be found by entering http://, followed by biotools.idtdna.com/antisense/AntiSense.aspx, which will provide appropriate antisense sequences for nucleic acid sequences up to 10,000 nucleotides in length. Using this program with the sEH gene provides the following exemplar sequences:

```
1) UGUCCAGUGCCCACAGUCCU       (SEQ ID NO: 34)

2) UUCCCACCUGACACGACUCU       (SEQ ID NO: 35)

3) GUUCAGCCUCAGCCACUCCU       (SEQ ID NO: 36)
```

-continued
```
4) AGUCCUCCCGCUUCACAGA        (SEQ ID NO: 37)

5) GCCCACUUCCAGUUCCUUUCC      (SEQ ID NO: 38)
```

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-β-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found by entering "www." followed by "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(10:4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol. Chem. 279(40):42230-9 (2004); Ying and Lin, Biochem Biophys Res Commun. 326(3):515-20 (2005).

Therapeutic Administration

EETs and inhibitors of sEH can be prepared and administered in a wide variety of oral, parenteral and aerosol formulations. In some preferred forms, compounds for use in the methods of the present invention can be administered by injection, that is, intravenously, intramuscularly, intracutaneously, subcutaneously, intraduodenally, or intraperitoneally, while in others, they are administered orally. The sEH inhibitor or EETs, or both, can also be administered by inhalation. Additionally, the sEH inhibitors, or EETs, or both, can be administered transdermally. Accordingly, the methods of the invention permit administration of pharmaceutical compositions comprising a pharmaceutically acceptable carrier or excipient and either a selected inhibitor or a pharmaceutically acceptable salt of the inhibitor.

For preparing pharmaceutical compositions from sEH inhibitors, or EETs, or both, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount of the sEH inhibitor, or EETs, or both, is employed in inhibiting cardiac arrhythmia or inhibiting or reversing cardiac hypertrophy or dilated cardiomyopathy. The dosage of the specific compound for treatment depends on many factors that are well known to those skilled in the art. They include for example, the route of administration and the potency of the particular compound. An exemplary dose is from about 0.001 μM/kg to about 100 mg/kg body weight of the mammal.

EETs are unstable in acidic conditions, and can be converted to DHETs. To avoid conversion of orally administered EETs to DHETs under the acidic conditions present in the stomach, EETs can be administered intravenously, by injection, or by aerosol. EETs intended for oral administration can be encapsulated in a coating that protects the EETs during passage through the stomach. For example, the EETs can be provided with a so-called "enteric" coating, such as those used for some brands of aspirin, or embedded in a formulation. Such enteric coatings and formulations are well known in the art. In some formulations, the EETs, or a combination of the EETs and an sEH inhibitor are embedded in a slow-release formulation to facilitate administration of the agents over time.

In another set of embodiments, an sEH inhibitor, one or more EETs, or both an sEH inhibitor and an EET are administered by delivery to the nose or to the lung. Intranasal and pulmonary delivery are considered to be ways drugs can be rapidly introduced into an organism. Devices for delivering drugs intranasally or to the lungs are well known in the art. The devices typically deliver either an aerosol of an therapeutically active agent in a solution, or a dry powder of the agent. To aid in providing reproducible dosages of the agent, dry powder formulations often include substantial amounts of excipients, such as polysaccharides, as bulking agents.

Detailed information about the delivery of therapeutically active agents in the form of aerosols or as powders is available in the art. For example, the Center for Drug Evaluation and Research ("CDER") of the U.S. Food and Drug Administration provides detailed guidance in a publication entitled: "Guidance for Industry: Nasal Spray and Inhalation Solution, Suspension, and Spray Drug Products—Chemistry, Manufacturing, and Controls Documentation" (Office of Training and Communications, Division of Drug Information, CDER, FDA, July 2002). This guidance is available in written form from CDER, or can be found on-line by entering "http://www." followed by "fda.gov/cder/guidance/4234fnl.htm". The FDA has also made detailed draft guidance available on dry powder inhalers and metered dose inhalers. See, Metered Dose Inhaler (MDI) and Dry Powder Inhaler (DPI) Drug Products—Chemistry, Manufacturing, and Controls Documentation, 63 Fed. Reg. 64270, (November 1998). A number of inhalers are commercially available, for example, to administer albuterol to asthma patients, and can be used instead in the methods of the present invention to administer the sEH inhibitor, EET, or a combination of the two agents to subjects in need thereof.

In some aspects of the invention, the sEH inhibitor, EET, or combination thereof, is dissolved or suspended in a suitable solvent, such as water, ethanol, or saline, and administered by nebulization. A nebulizer produces an aerosol of fine particles by breaking a fluid into fine droplets and dispersing them into a flowing stream of gas. Medical nebulizers are designed to convert water or aqueous solutions or colloidal suspensions to aerosols of fine, inhalable droplets that can enter the lungs of a patient during inhalation and deposit on the surface of the respiratory airways. Typical pneumatic (compressed gas) medical nebulizers develop approximately 15 to 30 microliters of aerosol per liter of gas in finely divided droplets with volume or mass median diameters in the respirable range of 2 to 4 micrometers. Predominantly, water or saline solutions are used with low solute concentrations, typically ranging from 1.0 to 5.0 mg/mL.

Nebulizers for delivering an aerosolized solution to the lungs are commercially available from a number of sources, including the AERx™ (Aradigm Corp., Hayward, Calif.) and the Acorn II® (Vital Signs Inc., Totowa, N.J.).

Metered dose inhalers are also known and available. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; and 4,896,832.

The formulations may also be delivered using a dry powder inhaler (DPI), i.e., an inhaler device that utilizes the patient's inhaled breath as a vehicle to transport the dry powder drug to the lungs. Such devices are described in, for example, U.S. Pat. Nos. 5,458,135; 5,740,794; and 5,785,049. When administered using a device of this type, the powder is contained in a receptacle having a puncturable lid or other access surface, preferably a blister package or cartridge, where the receptacle may contain a single dosage unit or multiple dosage units.

Other dry powder dispersion devices for pulmonary administration of dry powders include those described in Newell, European Patent No. EP 129985; in Hodson, European Patent No. EP 472598, in Cocozza, European Patent No. EP 467172, and in Lloyd, U.S. Pat. Nos. 5,522,385; 4,668,281; 4,667,668; and 4,805,811. Dry powders may also be delivered using a pressurized, metered dose inhaler (MDI) containing a solution or suspension of drug in a pharmaceutically inert liquid propellant, e.g., a chlorofluorocarbon or fluorocarbon, as described in U.S. Pat. Nos. 5,320,094 and 5,672,581.

Without further elaboration, it is believed that one skilled in the art can, using the preceding description, practice the present invention to its fullest extent.

EXAMPLES

Example 1

Inflammatory pain model: The nociception response was measured using the hind paw withdrawal latency test modified after Hargreaves at al., Pain, 32(1):77-88 (1988). Male Sprague-Dowley rats weighing 240-260 g, are individually housed at UC Davis Animal Resource Facility under standard conditions with free access to food and water, and maintained for at least 1 week before the experiments. On the day of the experiments, the animals' basal response is measured and then compounds are topically administered preceding an injection with 10 ug of endotoxin (1Lipopolysaccharide, "LPS", Sigma-Aldrich, St. Louis, Mo.). Nociceptive response is then measured at 120 minutes post-LPS injection. Compounds are formulated by dissolving them in ethanol and mixing with cream in a ratio of 1:8. Eight animals per group are used. A dose response curve is obtained by administering increasing concentrations of EETs and measuring nociceptive response.

Example 2

To determine the cellular receptors for EETs, in vitro bioassays were conducted using human receptors. From 150 available human receptors, 47 were selected on the basis of behavioral observations of animals when EETs were administered to them. These 47 selected human molecular receptors were screened using radio-ligand competition assays to identify potential receptors for EETs. The biological outcome of impacting these receptors was compared with the observed behavior to include each receptor into the screen. Based on the results of initial screening, efforts were focused on individual receptors, which were screened with each of the four regio-isomers of EETs. Several receptors and EET isomers were ruled out as not exhibiting activity.

Receptor Binding Experiments

Standard radio-ligand binding competition experiments were conducted on 47 human receptors using a final concentration of 10 μM. Percent inhibition of a known potent agonist was reported. The threshold for defining a "positive" hit was set as 25% inhibition of binding. Receptors which were inhibited by more than 25% in the first screen were further investigated by conducting the binding experiments using individual isomers of EETs.

Example 3

Bioassays. When animals are treated with lipopolysaccharide (LPS), they show a drastic reduction in their withdrawal latencies in pain response assays. The pain response, however, was restored towards the baseline levels with the application of increasing concentrations of EETs (doses 50,200 and 300 mg/kg).

Analgesic effect of EETs. LPS treatment produces hyperalgesia by reducing the baseline withdrawal latency by two fold. Animals topically administered EETs display significantly less hyperaigesia and their nociceptive response remains at the baseline level.

Receptor Binding Assays

As noted in the preceding Examples, first round screens were conducted using 47 human receptors. The receptors were expressed in recombinant mammalian cells. Only the receptors that were significantly inhibited by 10 pM of EETs are reported. Related receptor subtypes, however, are also included in Table 2 to emphasize specificity of EETs to the labeled receptors. In a second round of screens, the receptors that gave positive hits in the first round were selected and screened against each of the four regioisomers of EETs. This experiment was done with 3 μM of EETs to increase the stringency of the screen. The results are summarized in Table 3. The activity observed on Dopamine D3 receptor was lost in the second round. However significant inhibition of peripheral benzodiazepine receptors was observed with three of the four isomers of EETs (Table 2). Additionally 5,6-EET remained to have the same level of activity on Cannabinoid CB2 and Neurokinin NK2 receptors. Tables 2 and 3 present the early data we developed, while Table 4 presents more complete data.

TABLE 2

Screening of human receptors against a mixture of EETs.

| Receptor | % Inhibition of Control Specific Binding | Reference Compound | IC50 Ref (M) |
|---|---|---|---|
| BZD (peripheral) | 78 | PK11195 | 2.70E−09 |
| BZD (central) | 12 | diazepam | 1.00E−08 |
| Cannabinoid CB1 | 13 | CPS6940 | 1.00E−09 |
| Cannabinoid C62 | 26 | WIN55212-2 | 7.60E−09 |
| Dopamine D1 | 20 | SCH23390 | 4.80E−10 |
| Dopamine D2S | 16 | (+)butaclamol | 4.40E−09 |
| Dopamine D3 | 47 | (+)butaelamol | 8.90E−09 |
| Neurokinin NK1 | 12 | [Sar9,Met(02)11]-SP | 2.20E−10 |
| Neurokinin NK2 | 32 | [Nie10]-NKA(4-10) | 9.30E−09 |
| Neurokinin NK3 | 1 | SB 222200 | 1.00E−08 |

TABLE 3

Second round of screening using individual EET isomers on receptors that were significantly inhibited by a mixture of EETs in first screen.

| Receptor | Test Compound | % Inhibition of Control Specific Binding | Reference Compound | IC50 Ref (M) |
|---|---|---|---|---|
| BZD (peripheral) | 5,6-EET | 27 | PK11195 | 2.5E−09 |
| BZD (peripheral) | 8,9-EET | 11 | PK11196 | 2.5E−09 |
| BZD (peripheral) | 11,12-EET | 28 | PK11195 | 2.5E−09 |
| BZD (peripheral) | 14,15-EET | 45 | PK11195 | 2.5E−09 |
| Cannabinoid CB2 | 5,6-EET | 25 | WINS5212-2 | 2.7E−09 |
| Cannabinoid CB2 | 8,9-EET | −2 | WING5212-2 | 2.7E−09 |
| Cannabinoid CB2 | 11,12-EET | 3 | WINS5212-2 | 2.7E−09 |
| Cannabinoid CB2 | 14,15-EET | 5 | WIN55212-2 | 2.7E−09 |
| Dopamine D3 | 5,6-EET | 18 | (+)butaclamol | 8.7E−09 |
| Dopamine D3 | 8,9-EET | 9 | (+)butaclamol | 8.7E−09 |
| Dopamine D3 | 11,12-EET | 6 | (+)butaclamol | 8.7E−09 |
| Dopamine D3 | 14,15-EET | 10 | (+)butaclamol | 8.7E−09 |
| Neurokinin NK2 | 5,6-EET | 25 | [Nle10]-NKA(4.10) | 9.7E−09 |
| Neurokinin NK2 | 8,9-EET | 10 | [Nle101-NKA(4-10) | 9.7E−09 |
| Neurokinin $NK_2$ | 11,12-EET | 1 | [Nle10]-NKA(4-10) | 9.7E−09 |
| Neurokinin $NK_2$ | 14,15-EET | 8 | [Nle10]-NKA(4-10) | 9.7E−09 |

TABLE 4

Interaction of EETs with selected cellular receptors

| | $CB_1$ | $CB_2$ | $NK_1$ | $NK_2$ | $NK_3$ | Peripheral benzodiazepine | Central benzodiazepine | $D_3$ |
|---|---|---|---|---|---|---|---|---|
| EET-me mixture (μM) | >100 | 19 | >100 | 14 | >100 | 4.6 | >100 | 30 |
| 5,6 EET-me (μM) | NT | 20 | NT | 36 | NT | 12 | NT | >100 |
| 8,9 EET-me (μM) | NT | >100 | NT | >100 | NT | >100 | NT | >100 |
| 11,12 EET-me (μM) | NT | >100 | NT | >100 | NT | 140 | NT | >100 |
| 14,15 EET-me (μM) | NT | >100 | NT | >100 | NT | 12 | NT | >100 |

Binding assays were conducted by CEREP according to standardized procedures. A mixture of regioisomers of EETs were initially screened broadly for displacing ability of high affinity ligands. In a second round the $IC_{50}$ of the mixture and the individual isomers were determined. Reference compounds and their affinities (M) for respective receptors from left to right were CP 55940 (1.00E-09), WIN 55212-2 (7.60E-09), [Sar9,Met(O2)11]-SP (2.20E-0), [N1e10]-NKA(4-10) (9.30E-9), SB 222200 (1.00E-8), PK 11195 (2.70E-9), Diazepam (1.0E-08), (+) butaclamol (8.90E-09). NT: not tested.

Example 4

Receptor Binding Assays

Receptor binding experiments were contracted to CEREP (Redmond, Wash.). Compounds with encrypted identities were mailed to CEREP. Standard radio-ligand binding competition experiments were conducted initially on 47 receptors using a final concentration of 10 μM. Percent inhibition of a known potent agonist was reported. The threshold for a positive hit was set as 25% inhibition of binding by CEREP. Receptors which were inhibited at more than 25% in the first screen were further investigated by conducting the binding experiments using individual isomers of EETs.

(1) PBR Binding Assays

For the peripheral benzodiazepine assay, the procedure of Le Fur et al. (Life Sci. 33: 449-457 (1983)) was followed. Briefly, male Sprague-Dawley rats (200 g, Charles River Laboratories, Inc., Wilmington, Mass.) were sacrificed and hearts were excised. The ventricular tissue was homogenized (1:4 w/v) in cold sucrose (0.25 M), Tris HCl (5 mM, $MgCl_2$ (1 mM) buffer at pH 7.4. The homogenates were then filtered through a double layer of cheese cloth and centrifuged at 1,000×g for 10 minutes. The supernatant was recentrifuged at 40,000×g for 30 minutes. The resulting pellet was resuspended in the incubation buffer. The binding assays were performed in 50 mM Tris HCl, $MgCl_2$ 10 mM buffer pH 7.5 in a final volume of 1 ml containing 0.2 mg of cardiac membrane protein and the radioactive ligand, [$^3$H] PK 11195 (1-(2-chlorophenyl)-N-methyl-N-(1-methylpropyl)-1-isoquinoline carboxamide, a powerful PBR ligand) and increasing concentrations of EETs. After 15 minutes at 25° C., the membranes were filtered over GF/C filters (Whatman Inc., Florham Park, N.J.) followed by 3×5 ml washes with cold buffer. Specific binding (95% of total binding for both ligands) was defined as the amount of radioactivity displaced by 1 unlabelled R05-4864 (4'-chlorodiazepam), a ligand known to bind PBR. The radioactivity in the filters was measured with a scintillation counter. Equilibrium thermodynamic parameters of binding were determined utilizing classical thermodynamic equations.

(ii) CB2 Binding Assays

For CB2 binding assays, recombinant human receptor protein was expressed in Chinese Hamster Ovary (CHO) cells. The binding of the synthetic cannabinoid receptor agonist [$^3$H] WIN 55212-2 ((4,5-dihydro-2-methyl-4(4-morpholinylmethyl)-1-(1-naphthalenylcarbonyl)-6H-pyrrolo[3,2,1ij]quinolin-6-one) to cell membranes was determined by incubation of the ligand (0.8 nM) for 2 hours at 37° C. with cells in the cell culture buffer according to Munro et al. (Nature, 365:61-65 (1993)). EETs were added in increasing concentrations in parallel. The membranes were then filtered over GF/C filters (Whatman), followed by 3×5 ml washes with cold buffer. Specific binding (95% of total binding for both ligands) was defined as the amount of radioactivity displaced by 5 μM of unlabelled WIN 55212-2.

Example 5

Behavioral Nociceptive Testing

Behavioral nociceptive testing was conducted by assessing thermal hindpaw withdrawal latencies ("TWL") using a commercial Hargreaves (Hargreaves et al., A new and sensitive method for measuring thermal nociception in cutaneous hyperalgesia. Pain 32:77-88 (1988)) apparatus (IITC Life Science Inc., Woodland Hills, Calif.). Male Sprague-Dawley rats weighing 240-250 g, were individually housed at the UC Davis Animal Resource Facility under standard conditions with free access to food and water, and maintained for at least 1 week before the experiments. On the day of the experiment, the rats were transferred to a quiet room, acclimated for 1 h, and their baseline responses measured. In pilot experiments, the intensity of the thermal stimulus was set to produce a baseline TWL of 7-8 s. Following baseline measurements, rats were first treated with 200 μl of vehicle or compound-formulated cream by topical application to one hind paw. Compounds (including sEHI, steroid synthesis inhibitors, steroid receptor antagonists, and cannabinoid receptor antagonists, as shown in the Figure legends) were formulated by dissolving them in ethanol and mixing with Vanicream® (Pharmaceutical Specialties, Inc., Rochester, Minn.) in a ratio of 1:9. The cream was thoroughly massaged across the entire hind paw surface over a 2 min period. After 1.5 hours rats were treated with 200 μl of sEHI formulated cream. Within 10 min of sEHI application, lipopolysaccharide ("LPS", 10 μg in 50 μl 0.9% NaCl) was injected subcutaneously into the plantar surface of the treated paw. Immediately following LPS injection, animals were placed in acrylic chambers on a glass platform maintained at a temperature of 30±1° C. for TWL-measurement. During TWL measurement, a beam of radiant heat was focused onto the mid-portion of the plantar surface of the treated hind paw until the rat moved its stimulated hindpaw abruptly away from the heat stimulus. The duration of heat application necessary to elicit a withdrawal was designated as TWL. A maximum stimulus duration of 22 s was imposed to prevent tissue damage. Five TWL measurements were taken at 3-4 min interstimulus intervals for each of the time points following treatment. The three median TWLs were averaged for each animal at each time point.

Example 6

Fatty acids and lipid signaling: Lipid molecules are ubiquitous messengers that are known to participate in intracellular signaling, cell to cell communication and serve as neurotransmitters. Lipid messengers also regulate specific physiologic functions, one of which is the transmission of noxious sensory information (pain) in the periphery and the central nervous system. A significant aspect of the role of lipids in neuronal function is their ability to modify the functional responses of ion channels, synaptic transmission and cellular signaling cascades through which neuronal cell function is modified to meet physiologic demand (Sang, N. *Neuroscientist* 12:425-434 (2006); Chen, C. et al., *Prostaglandins & Other Lipid Mediators* 77:65-76 (2005)). Analysis of alterations in the type, amount and organization of lipids can provide critical information leading to the understanding of mechanism of action of each molecule, the early diagnosis of disease, identification of the mechanisms underlying the disease process itself and also can potentially provide an indication of efficacy of specific treatment regimes. For example it has recently become clear that, despite previous thinking, the kinetic characteristics of ion channels are intimately related to their dynamic interactions with their surrounding lipids and electric field-induced changes in protein—lipid interactions (De Petrocellis, L. et al., *Life Sciences* 77:1651-1666 (2005)). Thus, the lipid environment is now recognized as a direct modifier of the functional outcome of a transmitted electrical signal.

The arachidonic acid (AA) cascade is a relatively well exploited biological path with many therapeutic opportunities, only a limited number of which are taken advantage of. Moreover, there is evidence of the existence of parallel homologous cascades of other fatty acids, particularly a linoleic acid (LA) cascade. Although direct action of AA on various ionic currents has been demonstrated (Ordway, R. W. et al., *Science* 244:1176-1179 (1989)) the released AA is quickly converted to downstream metabolites by prostaglandin synthases, lipoxygenases and cytochrome P450 enzymes in a tissue- and context-dependent manner (Roman, R. *Metabolites of Arachidonic Acid in the Control of Cardiovascular Function Physiological Reviews* 82:131-185 (2002); Capdevila, J. et al., FASEB Journal 6:731-736 (1992); McGiff, J. C. *Annual Review of Pharmacology and Toxicology* 31:339-369 (1991)). Eicosanoids, the arachidonic acid-derived lipid mediators, are composed of several classes that include leukotrienes (LT), prostaglandins (PG), thromboxanes (TX), and hydroxy, epoxy and oxo-fatty acids. These eicosanoids are formed by various cells and most are thought to act locally (McGiff, J. C. *Annual Review of Pharmacology and Toxicology* 31:339-369 (1991); Imig, J. *Clinical Science* (London) 111:21-34 (2006)). Their biological roles include control of vascular tone, platelet aggregation, renal function, hypersensitivity and inflammation; thus, they are of great physiological importance. LA mono-epoxides (EpOMEs) and diols (DiHOMEs) also have many biological activities. For example, they induce vasodilatation and thus appear to regulate blood pressure (Ishizaki, T. et al., *Am Physiol* 268: 123-128 (1995)), may protect organisms from infectious diseases (Hayakawa, M. et al., *Biochem Biophys Res Commun* 137:424-430 (1986)), and may have a role in multiple-organ failure associated with severe burns, acute trauma, and respiratory distress syndrome (Hayakawa, M. et al., *Biochem Int* 21:573-579 (1990); Ozawa, T. et al., *Am Rev Respir Dis* 137:535-540 (1988); Kosaka, K. et al., *Mol Cell Biochem* 139:141-148 (1994)). EpOMEs may be endogenous chemical mediators regulating vascular permeability (Hennig, B. et al., *Metabolism* 49:1006-1013 (2000)).

Epoxy fatty acids and sEH: One of the metabolic fates of AA is the oxidation to EETs by cytochrome P450 epoxygenases. A multitude of interesting biological activities are found to be associated with the EETs using in vitro systems (Campbell, W. et al., *Circulation Research* 78:415-423 (1996)). Although EETs other than the 5,6-isomer are quite stable chemically, they are quickly degraded enzymatically with the sEH accounting in many cases for much of the metabolism. This rapid degradation has so far made it difficult to associate biological effects with the administration of EETs and other lipid epoxides particularly in vivo. Soluble epoxide hydrolase (sEH, EC 3.3.2.3), a alp fold hydrolytic enzyme that primarily hydrolyzes epoxides on acyclic systems, is the major enzyme that biodegrades EETs. By inhibiting sEH to increase the residence time of EETs, recently it has become clear that major roles of the EETs include but are not limited to modulation of blood pressure and modulation of inflammatory cascades (Spector, A. et al., *Progress in Lipid Research* 43:55-90 (2004); Node, K. et al., *Science* 285:1276-1279 (1999)). There are a number of other biological effects associated with the EETs, including neurohormone release, modulation of ion channel activity, cell proliferation, G-protein signaling and a variety of effects associated with modulation of NFκB (Spector, A. et al., *Progress in Lipid Research* 43:55-90 (2004); Node, K. et al., *Science* 285:1276-1279 (1999); Fleming, I. Hypertension 47:629-633 (2006); Feletou, M. et al., *Arteriosclerosis, Thrombosis, and Vascular Biology* 26:1215-1225 (2006)).

We have demonstrated a role of the EETs as modulated by sEH inhibitors (sEHIs) in reducing inflammatory pain (Inceoglu, B. et al., *Life Sciences* 79:2311-2319 (2006)). The array of biological effects observed with sEH inhibition illustrates the power of modulating the degradation of chemical mediators. Many of these biological effects can be modulated by sEHIs but presumably also by the natural eicosanoids and their mimics, all of which offer therapeutic potential. EETs and possibly other epoxy fatty acids are clearly regulatory molecules. By way of metabolic profiling of oxylipids and prostanoids, work in our laboratory has shown that blocking the COX and sEH branches simultaneously results in a synergistic decrease in prostaglandin production, and thus inflammation and pain, when a lipopolysaccharide (LPS)-elicited acute inflammatory model is used (Schmelzer, K. et al., *Proc Natl Acad Sci USA* 103:13646-13651 (2006) ("Schmelzer PNAS 2006"); Schmelzer, K. et al., *Proc Natl Acad Sci USA* 102:9772-9777 (2005)). Inhibition of sEH or COX 2 results in clear increases in EET concentrations. Our data implies that at least some of the effects of COX-2 inhibitors may be through an increase in EETs (Schmelzer PNAS 2006).

Steroidogenesis, AA, EETs, StAR and the peripheral benzodiazepine receptor: Steroid hormones are synthesized in steroidogenic cells of the adrenal, ovary, testis, placenta, and brain and are required for reproductive function and homeostasis. Acute steroidogenesis, regulated by trophic hormone stimulation, occurs on the order of minutes and is initiated by the mobilization and delivery of the substrate for all steroid hormone biosynthesis, cholesterol, from the outer to the inner mitochondrial membrane where it is metabolized to pregnenolone by the cytochrome P450 cholesterol side chain cleavage enzyme, P450scc (Payne, A. H. et al., *Overview of Steroidogenic Enzymes in the Pathway from Cholesterol to Active Steroid Hormones*, pp 947-970 (2004)).

The essential role of arachidonic acid (AA) in trophic hormone-stimulated steroidogenesis has been demonstrated starting in the early 1980s (Lin, T. Life Sciences 36:1255-1264 (1985) ("Lin 1985")). Various authors have suggested COX and LOX metabolites of AA were involved in the process (Lin 1985; Dix, C. J. et al., *The Biochemical Journal* 219:529-537 (1984); Mercure, F. et al., *General and Comparative Endocrinology* 102:130-140 (1996); Campbell, W. B. et al., *Journal Of Steroid Biochemistry* 24:865-870 (1986)). Stimulatory effects of the P450 branch, the epoxygenase products, on steroidogenesis were also reported in bovine adrenal cells early on (Nishimura, M. et al., *Prostaglandins* 38:413-430 (1989)). In human granulosa cells, low concentrations of EETs were reported to stimulate estradiol secretion (Van Voorhis, B. J. et al., *J Clin Endocrinol Metab* 76:1555-1559 (1993)). Recently, D. M. Stocco's group reported the identification of EETs as one of the factors that stimulate StAR (steroidogenic acute regulatory protein) expression and steroidogenesis (Wang, X. et al., *The involvement of epoxygenase metabolites of arachidonic acid in cAMP-stimulated steroidogenesis and steroidogenic acute regulatory protein gene expression*, pp 871-878 (2006)). StAR protein is one of the candidate proteins proposed as essential for steroidogenesis, possessing all the necessary characteristics of the acute regulator (Clark, B. J. et al., *Characterization of the steroidogenic acute regulatory protein (StAR)*, pp 28314-28322 (1994)). The acute response to hormonal stimulation has an absolute requirement for de novo protein synthesis (Davis, W. W. et al., *The Inhibitory Site Of Cycloheximide In The Pathway Of Steroid Biosynthesis*, pp 5153-5157 (1968); Garren, L. D. et al., *Studies on the Role of Protein Synthesis in the Regulation of Corticosterone Production by Adrenocorticotropic Hormone in vivo*, pp 1443-1450 (1965)). Inhibition of protein synthesis blocks hormone-induced steroid synthesis by blocking the delivery of cholesterol to the inner mitochondrial membrane (Farkash, Y. et al., *Endocrinology* 118:1353-1365 (1986)). Since activation of StAR protein expression is rapid and temporally related to steroid synthesis, the mRNA and protein quantities of StAR are good indicators of steroidogenesis.

Although a large body of literature exists on the actions of AA and its metabolites on steroid synthesis in the steroidogenic tissues, acute steroidogenesis in the nervous system is much less known but thought to proceed in parallel to that in steroidogenic cells (Furukawa, A. et al., *Steroidogenic Acute Regulatory Protein (StAR) Transcripts Constitutively Expressed in the Adult Rat Central Nervous System: Colocalization of StAR, Cytochrome P-450SCC (GYP XIA1), and 3beta-Hydroxysteroid Dehydrogenase in the Rat Brain*, pp 2231-2238 (1998)). In this regard, we have evidence that inhibition of sEH impacts steroidogenesis, presumably in the nervous tissues and that sEHI elicited analgesia is through acute modulation of steroidogenesis.

Another steroidogenesis regulating protein is the peripheral benzodiazepine receptor (PBR). As the biological roles of the PBR are emerging, the regulation of steroidogenesis among these roles (regulation of cellular proliferation, apoptosis, immunomodulation, porphyrin transport and heme biosynthesis) seems to predominate (Gavish, M. et al., *Receptor Pharmacological Reviews* 51:629-650 (1999); Papadopoulos, V. L. et al., *Neuroscience* 138:749-756 (2006)). Ligand binding to PBR results in the stimulation of mitochondrial pregnenolone formation (Mukhin, A. G. et al., *Mitochondrial Benzodiazepine Receptors Regulate Steroid Biosynthesis*, pp 9813-9816 (1989)). In addition, potent PBR ligands block inflammation profoundly in several distinct animal models of chronic inflammation (Torres, S. R. et al., *European Journal of Pharmacology* 408:199-211 (2000); Bressana, E. et al., *Life Sciences* 72:2591-2601 (2003)). Several inhibitors of steroid synthesizing enzymes can block the effects of PBR ligands (da Silva, M. et al., *Mediators of Inflammation* 13:93-103 (2004); Farges, R. et al., *Life Sciences* 74:1387-1395 (2004)).

Indeed Farges et al. showed that the P450scc inhibitor aminoglutethimide blocks the anti-inflammatory effects of PBR ligands in vivo (Farges, R. et al., *Life Sciences* 74:1387-1395 (2004)). The current proposed mode of action for this activity is that PBR complex, which includes StAR protein, VDAC (voltage dependent anion channel 1), PAP7, PKAR1a (cAMP-dependent protein kinase) and DBI (diazepam binding inhibitor) proteins, regulates steroid biosynthesis by facilitating the import of cholesterol from the outer to the inner mitochondrial membrane and that its acute modulation increases steroid and/or neurosteroid synthesis (Liu, J. et al., *Protein-Protein Interactions Mediate Mitochondrial Cholesterol Transport and Steroid Biosynthesis*, pp 38879-38893 (2006)). The import of cholesterol has long been recognized as the first and the rate limiting step in steroidogenesis (Papadopoulos, V. L. et al., *Neuroscience* 138:749-756 (2006); Bose, H. S. et al., *Nature* 417:87-91 (2002)). Both StAR and PBR proteins seem to be indispensable elements of the steroidogenic machinery and they function in a coordinated manner to transfer cholesterol into mitochondria (Hauet, T. et al., *Peripheral-Type Benzodiazepine Receptor-Mediated Action of Steroidogenic Acute Regulatory Protein on Cholesterol Entry into Leydig Cell Mitochondria*, pp 540-554 (2005); Stocco, D. M. et al., *Multiple Signaling Pathways Regulating Steroidogenesis and Steroidogenic Acute Regulatory Protein Expression: More Complicated than We Thought*, pp 2647-2659 (2005)). In addition, Hauet et al. proposed that PBR activation is required for StAR expression.

Cholesterol upon entering mitochondria is potentially directed to the synthesis of specific steroids in each tissue, which is dictated by the presence and activity of steroid synthesizing enzymes in a particular tissue. In fact, the differential expression and distribution of these enzymes is proposed to control the non-acute endogenous steroid tone. A change in the endogenous steroid tone through acute steroidogenesis may result with several favorable physiological outcomes including anxiolysis and analgesia, primarily through the actions of neurosteroids on GABAA conductance in the nervous tissue (Verleye, M. et al., *Pharmacology Biochemistry and Behavior* 82:712-720 (2005); Sanna, E. et al., *The Journal of Neuroscience* 24:6521-6530 (2004)). Neurosteroids 3α,5α-THPROG and 3α,5α-THDOC, for example are known to bind to and modulate GABAA channels which are inhibitory in nature and display anxiolytic, analgesic, anticonvulsant, sedative, hypnotic and anaesthetic properties (Belelli, D. et al., *Nature Reviews Neuroscience* 6:565-575 (2005)).

One of the most intriguing findings in respect to the role of EETs in inflammation was that EETs, through inhibiting NFκB, are anti-inflammatory (Node, K. et al., *Science* 285:1276-1279 (1999)). This also holds true in vivo in rats although EETs are algesic in the absence of inflammatory pain (Inceoglu, B. et al., *Life Sciences* 79:2311-2319 (2006)). As noted elsewhere herein, we found that EETs can displace high affinity radioligands from a number of cellular receptors previously not known to be associated with EETs, two of which are the mitochondrial or peripheral benzodiazepine receptor (PBR) and the CB2 receptor. Epoxy fatty acids and their increase in concentration or half life by way of sEH inhibition causes a favorable shift in the endogenous steroid tone through modulation of PBR and StAR, ultimately impacting GABAA channels and this is at least one of the mechanisms responsible for the observed powerful anti-inflammatory and/or analgesic effect of EETs and sEH inhibitors.

Pain, and neuropathy: Upon nerve damage the pro-inflammatory cytokines, specifically TNF-α is up regulated in surrounding tissues of nerves including the Schwann cells, mast cells and resident macrophages (Myers, R. R. et al., *Drug Discovery Today* 11:8-20 (2006)). This increase leads to a pathological process of progressive nerve degeneration which was recognized as early as 1850. Wallerian degeneration is highly correlated with the development of neuropathic pain (Stoll, G. et al., *Journal of the Peripheral Nervous System* 7:13-27 (2002)). Following nerve injury, nonresident macrophages in response to secreted chemotactic signals invade the injury site (Sommer, C. et al., *Neuroscience Letters* 270:25-28 (1999); Zelenka, M. et al., *Pain* 116:257-263 (2005)). This invasion and the process of nerve degeneration are temporally related to the peak periods of hyperalgesia in neuropathic pain (Shubayev, V. I. et al., *A spatial and temporal co-localization study in painful neuropathy*, pp 28-36 (2002)). Further migration of immune cells through the endothelium follows chemotactic signals that are released by injured nerves (Wagner, R. et al., *Neuroscience* 73:625-629 (1996)). Activated macrophages secrete components of the complement cascade, coagulation factors, proteases, hydrolases, interferons, TNF-α and other cytokines (Zelenka, M. et al., *Pain* 116:257-263 (2005)). Local TNF-α causes spontaneous electrophysiological activity in surviving nociceptive nerve fibers contributing to pain (Wagner, R. et al., *Neuroreport* 7:2897-2901 (1996)). Interestingly, the potential role of arachidonic acid metabolites have not systematically been investigated in the pathophysiology of neuropathic pain despite the fact that COX-2 inhibitors are quite effective in animal models of nerve injury (Bingham, S. et al., *Journal of Pharmacology and Experimental Therapeutics* 312:1161-1169 (2005); Ma, W. et al., *Brain Research* 937:94-99 (2002)). Moreover most animals studies that tested COX-2 inhibitors on neuropathic pain when the drug was given before or shortly following nerve injury showed encouraging results (Bingham, S. et al., *Journal of Pharmacology and Experimental Therapeutics* 312:1161-1169 (2005); De Vry, J. et al., *European J Pharmacology* 491:137-148 (2004)). Our limited mechanistic understanding of the pathways involved in neuropathic pain is clearly paralleled in the treatment of this condition. Currently, no single treatment options without significant side effects exist for neuropathic pain. A combination of pharmacological agents that block or attenuate the propagation of inflammation and potent analgesics are usually prescribed albeit with variable success (Gilron, I. et al., *Canadian Med Assn J* 175:265-275 (2006)).

The arachidonate cascade is the target for a significant fraction of the pharmaceuticals on the market and includes such NSAID drugs as salicylic acid, ibuprofen, naproxen, and celecoxib. We have found that sEHIs are more potent at reducing inflammatory eicosanoids in plasma than any of the above drugs (Schmelzer PNAS 2006). More importantly, NSAIDs shift arachidonic acid from one inflammatory cascade to another. In contrast, sEHI shift the blood eicosanoid profile from one propagating and expanding a pain response to one resolving pain toward a healthy state.

sEHIs and EETs are antinociceptive and analgesic in inflammatory pain models: Inhibition of sEH has been shown to result in a multitude of beneficial effects. One of these intriguing effects is that sEHIs protect mice from LPS elicited acute inflammation (Schmelzer, K. et al., *Proc Natl Acad Sci USA* 102:9772-9777 (2005)). LPS induced mortality, systemic hypotension, and histologically evaluated tissue injuries were substantially diminished by administration of urea-based, small-molecule inhibitors of sEH to mice. Moreover, sEH inhibitors decreased plasma levels of proinflammatory cytokines and nitric oxide metabolites while promoting the formation of lipoxins, thus supporting inflammatory resolution. These data suggest that sEHIs have therapeutic efficacy in the treatment and management of acute inflammatory diseases. The sEHI dependant reduction of prostanoid production in this model also suggests that inhibition of sEH may attenuate inflammatory pain. This is confirmed by using two distinct inflammatory pain models where we showed that inhibitors of sEH are antihyperalgesic.

Hyperalgesia in the LPS-elicited pain model was induced by intraplantar LPS injection and sEH inhibitors were delivered topically. We found that urea based sEHIs can successfully be delivered through the transdermal route. The maximal biological effect of sEHI AEPU also corresponds to the maximum plasma concentration and that sEH inhibitors effectively attenuate thermal hyperalgesia and mechanical allodynia in rats treated with LPS. In addition, we show that epoxydized arachidonic acid metabolites, EETs, are also effective in attenuating thermal hyperalgesia in this model. In parallel with the observed biological activity, metabolic analysis of oxylipids showed that inhibition of sEH resulted in a decrease in PGD2 levels and sEH generated degradation products of linoleic and arachidonic acid metabolites with a concomitant increase in epoxides of linoleic acid.

Using a second distinct inflammatory model, hyperalgesia was induced by intraplantar injection of 2% carrageenan (CAR) and sEH inhibitors were again delivered topically 20 hours post CAR injection. The sEHI AUDA-be blocked CAR induced local thermal hyperalgesia effectively. AUDA-be not only had a prophylactic effect in the LPS model, but was also effective therapeutically in reversing thermal hyperalgesia. These data show that inhibition of sEH may become a viable therapeutic strategy to attain analgesia.

EETs Act on PBR.

Although inhibition of sEH will decrease pain the mechanism of action of this effect is largely unknown. A current hypothesis is that inhibition of sEH leads to increased stability, hence residence time of natural EETs and that EETs are responsible for the observed biological activity. Therefore we subjected a mixture of regioisomers of EETs to a standard receptor screening using high affinity radioligands. This assay was conducted by a contract research organization (CEREP). We selected a subset of 48 cellular receptors based on the behaviors of the sEH knockout mice and sEHI treated rats. Four of these receptors were inhibited by EETs with micromolar affinities.

sEHI Elicited Analgesia is Blocked by Inhibition of Steroid/Neurosteroid Synthesis Based on the functions of PBR, we hypothesized that the interaction of EETs with this receptor may cause an increase in steroid production in the periphery and neurosteroid production in the brain. We used pharmacological inhibitors of steroid synthesis to test this hypothesis. Specifically, aminogluthetimide (AGL), effectively blocks all steroid synthesis by inhibiting the first enzyme, P450scc, in the steroid synthesis pathway. When topically administered to rats, AGL completely blocked the antihyperalgesic action of sEHI AEPU in the LPS-elicited inflammatory pain model. We selected AEPU for these tests because AEPU is less likely to be an EET mimic than are some other sEHI, in particular AUDA-be, because of its structural properties (i.e. the polyglycol secondary pharmacophore). Additionally, another inhibitor, finasteride, blocks 5α reductase and stops the steroid biosynthesis by blocking the conversion of testosterone to dihydrotestosterone in the case of steroids and the conversion of progesterone to allopregnanolone in the case of neurosteroids. Finasteride also blocked the anti-hyperalgesic activity of AEPU. In contrast, however, a non-steroidal estrogen receptor antagonist, tamoxifen, a dual progesterone/glucocorticoid receptor antagonist, mifepristone, an androgen receptor antagonist, nilutamide, and an aldosterone receptor antagonist, spironoloactone, did not have any impact on the antihyperalgesic action of AEPU, indicating that sEHIs and/or EETs are not acting through these steroid receptors.

Figure 3:
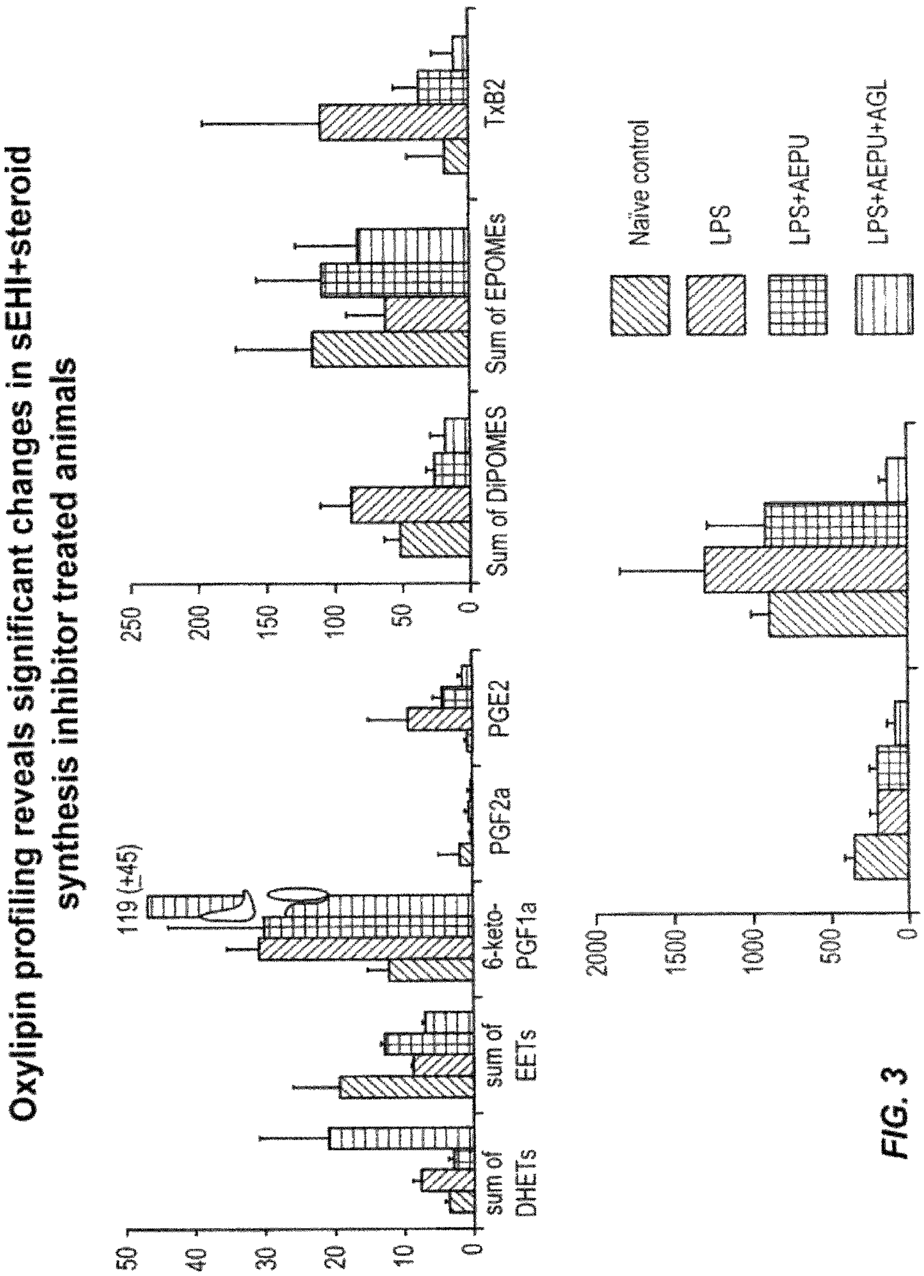
FIGS. 3A-3C are graphs depicting metabolomic analyses of oxylipids and prostaglandins, revealing that there are significant differences in animals treated with sEH inhibitors and with an sEH inhibitor and a steroid synthesis inhibitor. For each Figure, the Y axis shows a scale in ng/mL for the bars set forth in the Figure, while the X axis shows the amounts of various metabolites, as indicated below the axis.

As shown in FIG. 3, oxylipin analysis from animals in these tests showed that the PGE2 levels did not correlate well with the LPS elicited thermal hyperalgesia bioassay in animals treated with steroid synthesis inhibitor+sEHI. For example PGE2 levels were significantly lower in animals that received AGL+LPS+AEPU than in animals treated with AEPU+LPS or LPS only, whereas these animals were clearly hyperalgesic despite the administration of AEPU. See, FIG. 3. This means that inhibition of sEH is not only effective against inflammatory pain but also effective in other types of pain that are not necessarily modulated by prostanoid levels. Indeed, non-inflammatory types of pain are known to be not well addressed by COX inhibitors. The levels of EETs and DHETs, however, correlated well with the nociceptive end result. AGL significantly reduced levels of EETs and increased levels of DHETs in AGL+AEPU-administered animals compared to AEPU-administered animals, indicating that EETs are responsible for the anti-hyperalgesic activity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of relieving a condition selected from the group consisting of status epilepticus, other forms of epilepsy, symptoms of opiate withdrawal, insomnia, or mania in a subject in need thereof, said method comprising administering to said subject an effective amount of an agent or agents selected from the group consisting of a cis-epoxyeicosantrienoic acid ("EET"), an inhibitor of soluble epoxide hydrolase ("sEH"), and a combination of an EET and an inhibitor of sEH, wherein the inhibitor of sEH comprises a central pharmacophore comprising a urea, carbamate, or amide; and a carbamate, ester, carbonate or amide approximately 7.5 angstroms from the carbonyl of the central pharmacophore, thereby relieving said condition in said subject.

2. A method of claim 1, wherein the agent is an EET.

3. A method of claim 1, wherein the EET is selected from the group consisting of 14,15-EET, 8,9-EET, 11,12-EET or 5,6-EET.

4. A method of claim 1, wherein the agent is an inhibitor of sEH.

5. A method of claim 4, wherein the inhibitor of sEH inhibits sEH with an $IC_{50}$ of less than about 500 μM.

6. A method of claim 4, wherein the inhibitor of sEH inhibits sEH with an $IC_{50}$ of less than about 0.1 μM.

7. A method of claim 1, wherein the condition is status epilepticus or other forms of epilepsy.

8. A method of claim 1, wherein the inhibitor of sEH comprises a polyglycol secondary pharmacophore.

9. A method of claim 1, wherein the agent is administered orally.

10. A method of claim 1, wherein the agent is administered by inhalation.

11. A method of claim 1, wherein the agent is administered by intranasal or pulmonary delivery.

12. A method of relieving a condition selected from the group consisting of status epilepticus, other forms of epilepsy, symptoms of opiate withdrawal, insomnia, or mania in a subject in need thereof, said method comprising administering to said subject an effective amount of an agent or agents selected from the group consisting of a cis-epoxyeicosantrienoic acid ("EET"), an inhibitor of soluble epoxide hydrolase ("sEH"), and a combination of an EET and an inhibitor of sEH, wherein the inhibitor of sEH comprises a central pharmacophore comprising a urea, carbamate, or amide; a carbamate, ester, carbonate or amide approximately 7.5 angstroms from the carbonyl of the central pharmacophore; and inhibits sEH with an $IC_{50}$ of less than about 500 μM, thereby relieving said condition in said subject.

13. A method of claim 12, wherein the agent is an EET.

14. A method of claim 12, wherein the EET is selected from the group consisting of 14,15-EET, 8,9-EET, 11,12-EET or 5,6-EET.

15. A method of claim 12, wherein the agent is an inhibitor of sEH.

16. A method of claim 12, wherein the condition is status epilepticus or other forms of epilepsy.

17. A method of claim 12, wherein the inhibitor of sEH comprises a polyglycol secondary pharmacophore.

18. A method of claim 12, wherein the inhibitor of sEH inhibits sEH with an $IC_{50}$ of less than about 0.1 μM.

19. A method of claim 12, wherein the agent is administered by a route of administration selected from the group consisting of oral, inhalation, intranasal and pulmonary delivery.

* * * * *